(12) United States Patent
Fabian

(10) Patent No.: US 11,504,269 B2
(45) Date of Patent: Nov. 22, 2022

(54) THERAPEUTIC BRA

(71) Applicant: Jennifer L. Fabian, Mineral Wells, TX (US)

(72) Inventor: Jennifer L. Fabian, Mineral Wells, TX (US)

( * ) Notice: Subject to any disclaimer, the term of this patent is extended or adjusted under 35 U.S.C. 154(b) by 247 days.

(21) Appl. No.: 16/688,573

(22) Filed: Nov. 19, 2019

(65) Prior Publication Data

US 2021/0145633 A1    May 20, 2021

(51) Int. Cl.
*A61F 7/02* (2006.01)
*A41C 3/00* (2006.01)
*A61H 1/00* (2006.01)
*A61F 7/00* (2006.01)

(52) U.S. Cl.
CPC .............. *A61F 7/02* (2013.01); *A41C 3/0064* (2013.01); *A61H 1/00* (2013.01); *A61F 2007/0021* (2013.01); *A61F 2007/0074* (2013.01); *A61F 2007/0234* (2013.01); *A61H 2201/0207* (2013.01); *A61H 2201/165* (2013.01); *A61H 2205/082* (2013.01)

(58) Field of Classification Search
CPC ..... A61F 2007/0021; A61F 2007/0235; A41C 3/0064
See application file for complete search history.

(56) References Cited

U.S. PATENT DOCUMENTS

| | | |
|---|---|---|
| 3,632,966 A | 1/1972 | Arron |
| 5,235,972 A | 8/1993 | Strong |
| 5,235,974 A * | 8/1993 | Miller ..................... A61F 7/007 |
| | | 219/211 |
| 5,679,052 A | 10/1997 | Rucki |
| 6,210,771 B1 | 4/2001 | Post et al. |
| 6,439,942 B1 | 8/2002 | Pillai et al. |
| 6,464,717 B1 | 10/2002 | Smith et al. |

(Continued)

FOREIGN PATENT DOCUMENTS

| | | |
|---|---|---|
| AU | 4685899 A1 | 1/2001 |
| CA | 2280456 A1 | 2/2001 |

(Continued)

OTHER PUBLICATIONS

Anatomy and Physiology; Ch. 7 Axial Skeleton; 7.4 The Thoracic Cage; downloaded Oct. 28, 2019.

(Continued)

*Primary Examiner* — Kaitlyn E Smith

(57) ABSTRACT

A therapeutic bra including a body portion having a front, a back, a first side, second side, a first cup, and a second cup; the front and the back are connected at the first and second sides, the first cup including a first opening for receiving a first nipple of a user therethrough; the second cup including a second opening for receiving a second nipple of the user therethrough; a flap coupled to the first cup and configured to selectively conceal or expose the first opening; a second flap coupled to the second cup and configured to selectively conceal or expose the second opening; and a first heating apparatus comprising a first heating loop operably connected to a power source and a controller disposed on the body portion; and first and second heating loops associated with the respective cup, the side, the front, and/or flap.

20 Claims, 22 Drawing Sheets

(56) References Cited

U.S. PATENT DOCUMENTS

| | | |
|---|---|---|
| 7,081,034 B1 | 7/2006 | Zoellner |
| 7,115,842 B2 | 10/2006 | Keane |
| 7,448,090 B2 | 11/2008 | Lucock |
| 7,878,880 B2 | 2/2011 | Hendrickson |
| 8,192,247 B2 | 6/2012 | Abbaszadeh |
| 8,307,463 B2 | 11/2012 | Ritchie |
| 8,323,070 B2 | 12/2012 | Abbaszadeh |
| 8,414,353 B1 | 4/2013 | Leavell |
| 8,506,347 B2 | 8/2013 | Clair et al. |
| 9,364,030 B1* | 6/2016 | Aiello ............ H04W 4/80 |
| 9,781,954 B1 | 10/2017 | Osetek et al. |
| 10,166,148 B2 | 1/2019 | Dunn |
| 10,201,195 B1 | 2/2019 | Khaliuta et al. |
| 10,231,308 B2 | 3/2019 | Zlotnikov et al. |
| 10,231,492 B1 | 3/2019 | Bastug |
| 2003/0224685 A1 | 12/2003 | Sharma |
| 2006/0234584 A1 | 10/2006 | Valentine |
| 2007/0078324 A1 | 4/2007 | Wijisiriwardana |
| 2008/0223844 A1* | 9/2008 | Cronn ............ A41D 19/01535 |
| | | 219/211 |
| 2011/0092134 A1 | 4/2011 | Alva |
| 2012/0171930 A1 | 7/2012 | Kaufman |
| 2014/0088199 A1 | 3/2014 | Sharma |
| 2017/0056644 A1* | 3/2017 | Chahine ............ A61F 7/02 |
| 2017/0258628 A1* | 9/2017 | Awasthi ............ A61F 7/007 |
| 2018/0103691 A1* | 4/2018 | Alva ............ A41C 3/04 |
| 2018/0193185 A1* | 7/2018 | Thomas ............ A61F 7/02 |
| 2018/0255840 A1 | 9/2018 | Abbaszadeh |
| 2018/0352873 A1 | 12/2018 | Miller et al. |
| 2018/0369064 A1 | 12/2018 | Baxter et al. |
| 2019/0000152 A1 | 1/2019 | Fletcher |
| 2019/0014829 A1* | 1/2019 | Kim ............ A41C 3/0007 |
| 2019/0037931 A1 | 2/2019 | Akerson et al. |
| 2019/0040554 A1 | 2/2019 | Pidwerbecki et al. |
| 2019/0240109 A1* | 8/2019 | Barkay ............ A41C 3/005 |

FOREIGN PATENT DOCUMENTS

| | | |
|---|---|---|
| CN | 2576027 Y | 10/2003 |
| CN | 2643859 Y | 9/2004 |
| CN | 1650766 A | 8/2005 |
| CN | 201790937 U | 4/2011 |
| CN | 202104233 U | 1/2012 |
| CN | 202311204 U | 7/2012 |
| CN | 202436124 U | 9/2012 |
| CN | 102771906 A | 11/2012 |
| CN | 202566324 U | 12/2012 |
| CN | 203598190 U | 5/2014 |
| CN | 204048060 U | 12/2014 |
| CN | 204306046 U | 5/2015 |
| CN | 104872832 A | 9/2015 |
| CN | 105124787 A | 12/2015 |
| CN | 105411016 A | 3/2016 |
| CN | 106580683 A | 4/2017 |
| CN | 206534138 U | 10/2017 |
| CN | 107647961 A | 2/2018 |
| CN | 108402536 A | 8/2018 |
| EP | 0263041 A2 | 4/1988 |
| WO | 0076433 A1 | 12/2000 |
| WO | 03087451 A2 | 10/2003 |
| WO | 03094717 A1 | 11/2003 |
| WO | 2004069120 A1 | 8/2004 |
| WO | 2007040878 A1 | 4/2007 |

OTHER PUBLICATIONS

Berens et al.; ABM Clinical Protocol #26: Persistent Pain with Breastfeeding; Breastfeeding Medicine; vol. 11, No. 2, 2016.
Robbins et al.; Women's Imaging—Original Research; Accuracy of Diagnostic Mammography and Breast Ultrasound During Pregnancy and Lactaion; Mar. 2011.
DeFilippis et al.; Women's Imaging—Review; The ABCs of Accessory Breast Tissue: Basic Information Every Radiologist Should Know; May 2014.
Rivard et al.; Anatomy, Thorax, Breast—StatPearls—MCBI Bookshelf; downloaded Oct. 28, 2019.
Amir et al.; ABM Clinical Protocol #4: Mastitis, Revised Mar. 2014; Breastfeeding Medicine; vol. 8, No. 5, 2014.
Breastfeeding and the Use of Human Milk; American Academy of Pediatrics; vol. 129, No. 3, Mar. 2012.
Berens et al.; ABM Clinical Protocol #20: Engorgement, Revised 2016; Breastfeeding Medicine; vol. 11, No. 4, 2016.
Zucca-Matthes et al.; Anatomy of the nipple and breast ducts; Accepted May 5, 2015; Glad Surgery 2016, 5(1).
Moran et al.; From Folklore to Scientific Evidence: Breast-Feeding and Wet-Nursing in Islam and the Case of Non-Puerperal Lactation; International Journal of Biomedical Science, vol. 3, No. 4, Dec. 2007.
Geddes; The anatomy of the lactating breast: Latest research and clinical implications; Infant, vol. 3, Issue 2, 2007.
Ramsay et al.; Anatomy of the lactating human breast redefinded with ultrasound imaging; J.Anat. (2005) 206.
Mastitis While Breastfeeding; Michigan Medicine; downloaded Oct. 28, 2019.
Zelazniewicz et al.; Maternal breast volume in pregnancy and lactation capacity; Accepted Sep. 30, 2018; Am J Phys Anthropol. 2019; 168.
Elad et al.; Biomechanics of milk extraction during breast-feeding; PNAS, vol. 111, No. 14, Apr. 8, 2014.
Holanda et al.; Ultrasound findings of the physiological changes and most common breast diseases during pregnancy and lactation; Radiol Bras. Nov./Dec. 2016; 49(6).
Hamilton et al.; Births: Provisional Data for 2017; Vital Statistics Rapid Release; Report No. 004, May 2018.
Li et al.; Why Mothers Stop Breastfeeding: Mothers' Self-reported Reasons for Stopping During the First Year; Pediatrics vol. 122, Supplement 2, Oct. 2008.

* cited by examiner

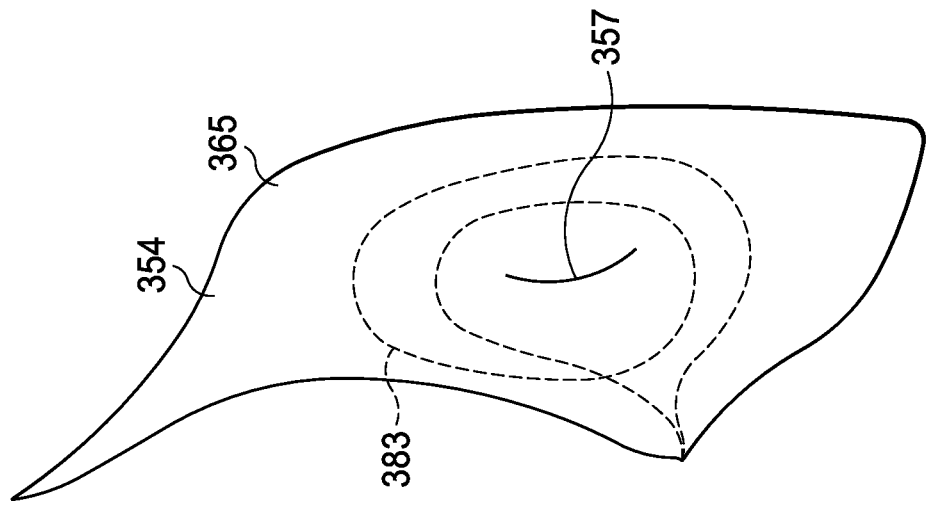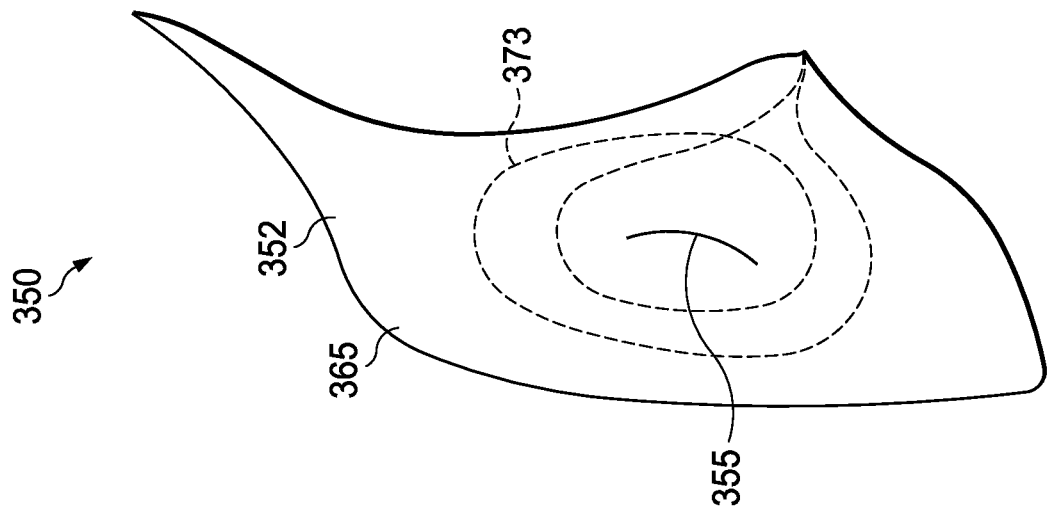
FIG. 8C

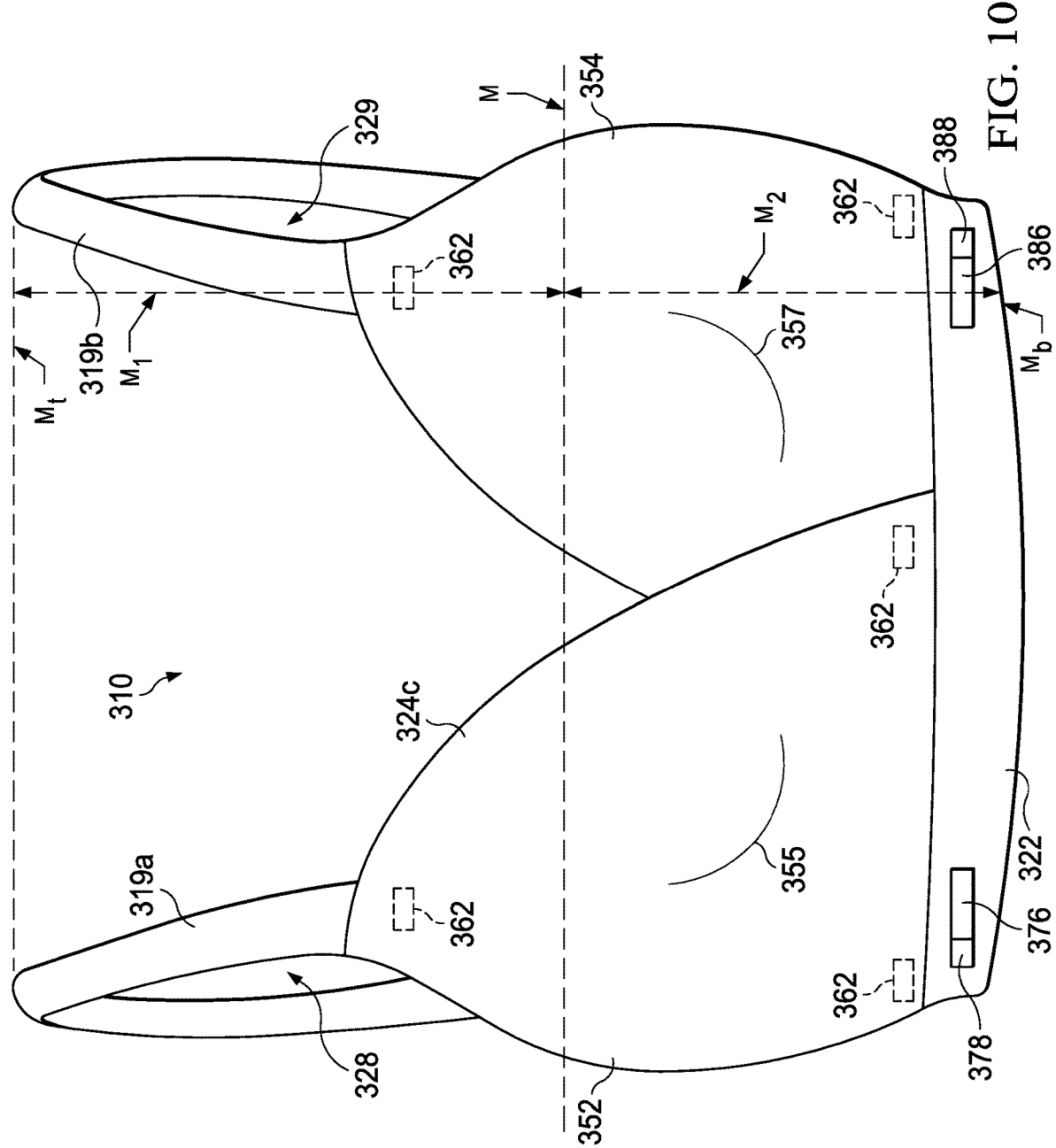

THERAPEUTIC BRA

BACKGROUND

Technical Field

The present disclosure relates to therapeutic treatment systems, and more particularly, to therapeutic bras for applying heat and/or vibration to breast tissue.

Description of Related Art

Clinical studies and practice have shown that applying heat to tissue accelerates tissue healing and alleviates pain and discomfort by stimulating circulation and increasing tissue elasticity.

The applications of heat therapy are numerous, but application of heat therapy has been particularly successful in assisting in the prevention, treatment, and recovery of mastitis, engorgement, clogged ducts, nipple vasospasm, slow let down, low milk supply, and alleviating overall pain and discomfort associated with nursing, pumping, and weaning.

Breast tissue consists of four quadrants and tail of spence. The location of breast tissue on the body extends from the second rib, just below the clavicle, to the sixth rib. The tail of spence space extends into the under arm and is also referred to as Spence's tail, axillary process, axillary tail). During pregnancy and lactation the hormones released cause the breast tissue to expand and fill these spaces.

While the clinical benefits of applying heat therapy are widely known, there is a need for an improved therapeutic bra that may benefit healthcare providers and patients.

SUMMARY OF THE INVENTION

In a first aspect, there is provided a therapeutic bra including a body portion configured to fit around a back and chest of the user; the body portion having a front, a back, a first side, a second side, a first cup, and a second cup; the front and the back are connected at the first and second sides, the body portion extends circumferentially around the back and chest of the user, the first cup disposed on the front of the body portion, the first cup including a first opening for receiving a first nipple of a user therethrough; the second cup disposed on the front of the body portion, the second cup including a second opening for receiving a second nipple of the user therethrough; a first flap coupled to the front and configured to selectively conceal or expose the first opening; a second flap coupled to the front and configured to selectively conceal or expose the second opening; a first heating apparatus comprising: a first power source disposed on the body portion; a first controller disposed on the body portion; and a first heating loop associated operably connected to the first power source and the first controller; the first heating loop associated with the first cup, the first side, the front, and/or first flap; a second heating apparatus comprising: a second power source disposed on the body portion; a second controller disposed on the body portion; and a second heating loop operably connected to the second power source and the second controller; the second heating loop associated with the second cup, the second side, the front, and/or second flap; wherein the user can operate the first heating loop and the second loop simultaneously and/or independently.

In an embodiment, the first and second heating loops are each comprised of an electrically conductive fiber that is malleable and with a low profile.

In yet another embodiment, the electrically conductive fiber is at least one of the following: a nichrome resistance wire, a kanthal wire, a cupronickel alloy wire, a molybdenum disilicide wire, a positive temperature coefficient ceramic element, a conductive thread, and a carbon nanotube coated thread.

In an exemplary embodiment, at least one of the body, the first flap, and the second flap are comprised of a textile having a non-conductive fiber, the electrically conductive fibers of the first and second heating loops are stitched through the textile.

In some embodiments, the body, the first flap, and the second flap are each comprised of a multi-layer textile.

In yet another embodiment, the multilayer textile comprises an inner layer, an outer layer, and a center layer, and the first heating loop and/or the second heating loop is woven through at least one of the inner layer, the outer layer, and the center layer.

In an exemplary embodiment, first and second heating loops are woven through the center layer.

In still another embodiment, the bra is configured to have a full coverage neckline.

In an illustrative embodiment, the front of the body portion has a neckline defined by the first cup and the second cup and/or the first flap and the second flap.

In an embodiment, the neckline is adjustable.

In yet another embodiment, at least one of the first flap and the second flap includes a first slit and a second slit, respectively.

In still another embodiment, the therapeutic bra includes a plurality of vibrating devices associated with the front, the first side, the second side, the first flap, and/or the second flap, wherein each of the vibrating devices are operated simultaneously and/or independently.

In a second aspect, there is provided a therapeutic bra including a body portion configured to fit around a back and chest of the user; the body portion having a front, a back, a first side, a second side, a first cup, and a second cup; the front and the back are connected at the first and second sides, the body portion extends circumferentially around the back and chest of the user, the first cup disposed on the front of the body portion, the first cup including a first opening for receiving a first nipple of a user therethrough; the second cup disposed on the front of the body portion, the second cup including a second opening for receiving a second nipple of the user therethrough; a first flap coupled to the first cup and configured to selectively conceal or expose the first opening; a second flap coupled to the second cup and configured to selectively conceal or expose the second opening; a first heating apparatus comprising a first heating loop operably connected to a power source and a controller disposed on the body portion; the first heating loop associated with the first cup, the first side, the front, and/or the first flap; and a second heating apparatus comprising: a second heating loop operably connected to the power source and the controller; the second heating loop associated with the second cup, the second side, the front, and/or the second flap.

In another embodiment, at least one of the body, the first flap, and the second flap are comprised of a textile having a non-conductive fiber, the first and second heating loops each comprise an electrically conductive fiber stitched through the textile.

In some embodiments, the front of the body portion has a neckline defined by the first cup and the second cup and/or the first flap and the second flap, the neckline being adjustable.

In an illustrative embodiment, the bra further includes a plurality of vibrating devices associated with the front, the first side, the second side, the first flap, and/or the second flap.

In a third aspect, there is provided a therapeutic bra including a body portion configured to fit around a back and chest of the user; the body portion having a front, a back, a first side, and a second side; the front and the back are connected at the first and second sides, the body portion extends circumferentially around the back and chest of the user, a first flap coupled to the front of the body portion and configured to selectively conceal or expose the first opening; a second flap coupled to front of the body portion and configured to selectively conceal or expose the second opening; a first heating apparatus associated with the first flap, the first heating apparatus comprising: a first power source; a first controller; and a first heating loop operably connected to the first power source and the first controller; the first heating loop associated with the first flap; a second heating apparatus associated with the second flap, the second heating apparatus comprising: a second power source; a second controller; and a second heating loop operably connected to the second power source and the second controller; the second heating loop disposed within the second flap; wherein the use can operate the first heating loop and the second loop simultaneously and/or independently.

In an embodiment, the neckline is defined by the first flap and the second flap.

In some embodiments, the neckline is adjustable.

In an illustrative embodiment, the therapeutic bra includes a plurality of vibrating devices associated with the first flap and/or the second flap.

In a fourth aspect, there is provided a therapeutic bra including a body portion configured to fit around a back and chest of the user; the body portion having a front, a back, a first side, second side, a first cup, and a second cup; the front and the back are connected at the first and second sides, the body portion extends circumferentially around the back and chest of the user, the first cup disposed on the front of the body portion, the first cup including a first opening for receiving a first nipple of a user therethrough; the second cup disposed on the front of the body portion, the second cup including a second opening for receiving a second nipple of the user therethrough; a first flap coupled to the first cup and configured to selectively conceal or expose the first opening; a second flap coupled to the second cup and configured to selectively conceal or expose the second opening; a first heating apparatus comprising a first heating loop operably connected to a power source and a controller disposed on the body portion; the first heating loop associated with the first cup, the first side, the front, the first flap, the second cup, the second side, and/or the second flap.

In a fifth aspect, there is provided a therapeutic bra including a body portion configured to fit around a back and chest of the user; the body portion having a front, a back, a first side, second side, a first cup, and a second cup; the front and the back are connected at the first and second sides, the body portion extends circumferentially around the back and chest of the user, the first cup disposed on the front of the body portion, the first cup including a first opening for receiving a first nipple of a user therethrough; the second cup disposed on the front of the body portion, the second cup including a second opening for receiving a second nipple of the user therethrough; a first flap coupled to the first cup and configured to selectively conceal or expose the first and/or second openings; a first heating apparatus comprising a first heating loop operably connected to a power source and a controller disposed on the body portion; the first heating loop associated with the first cup, the first side, the front, the first flap, the second cup, the second side, and/or the second flap.

In a sixth aspect, there is provided a therapeutic bra including a body portion configured to fit around a back and chest of the user; the body portion having a front, a back, a first side, a second side, a first cup, and a second cup; the front and the back are connected at the first and second sides, the body portion extends circumferentially around the back and chest of the user; the first cup disposed on the front of the body portion, the first cup including a first opening for receiving a first nipple of a user therethrough; the second cup disposed on the front of the body portion, the second cup including a second opening for receiving a second nipple of the user therethrough; and a plurality of vibrating devices associated with the front.

In an embodiment, the therapeutic bra includes at least one flap disposed on the front of the body portion and configured to selectively conceal or expose the first and/or second opening. The therapeutic bra further includes at least one vibrating device associated with the at least one flap.

Other aspects, features, and advantages will become apparent from the following detailed description when taken in conjunction with the accompanying drawings, which are a part of this disclosure and which illustrate, by way of example, principles of the inventions disclosed.

DESCRIPTION OF THE DRAWINGS

FIGS. 8A-8C, 9 and 10 illustrate an exemplary embodiment of a therapeutic bra, FIGS. 8A and 8C schematically illustrate heating loops, FIG. 8B and illustrate fastening of the full coverage embodiment;

DESCRIPTION OF THE PREFERRED EMBODIMENT

Illustrative embodiments of a therapeutic bra and systems for such are described below. In the interest of clarity, all features of an actual implementation may not be described in this specification. It will of course be appreciated that in the development of any such actual embodiment, numerous implementation-specific decisions must be made to achieve the developer's specific goals, which may vary from one implementation to another. Moreover, it will be appreciated that such a development effort might be complex and time-consuming but would nevertheless be a routine undertaking for those of ordinary skill in the art having the benefit of this disclosure. The following description of example embodiments provides information that enables a person skilled in the art to make and use the subject matter set forth in the appended claims, but it may omit certain details already well-known in the art. The following detailed description is, therefore, to be taken as illustrative and not limiting.

In the specification, reference may be made to the spatial relationships between various components and to the spatial orientation of various aspects of components as the devices are depicted in the attached drawings. However, as will be recognized by those skilled in the art after a complete reading of the present application, the devices, members, apparatuses, etc. described herein may be positioned in any desired orientation. Thus, the use of terms such as "above," "below," "upper," "lower," or other like terms to describe a spatial relationship between various components or to describe the spatial orientation of aspects of such components should be understood to describe a relative relationship between the components or a spatial orientation of aspects of such components, respectively, as the device described herein may be oriented in any desired direction.

Figure 1A:
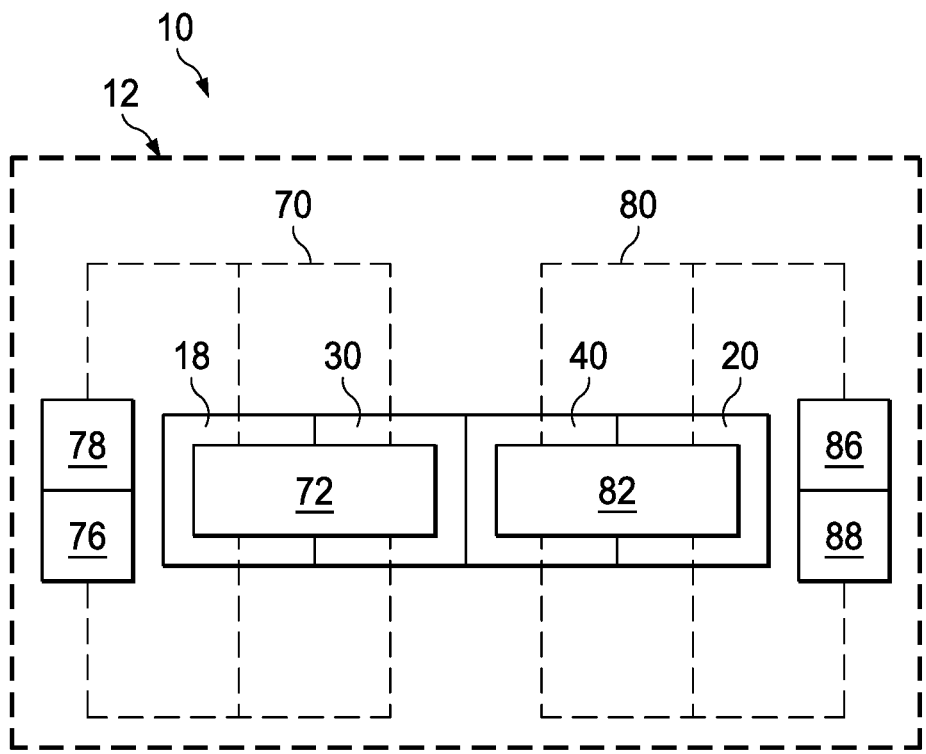
FIG. 1A is a functional block diagram of an embodiment of a therapeutic bra that can provide heat therapy in accordance with this specification.

FIG. 1A is a simplified functional block diagram of an example embodiment of a therapeutic bra 10 that can provide heat therapy to breast tissue in accordance with this specification.

The term "breast tissue," in this context broadly refers to the adipose, connective, and glandular tissues that overlie the pectoralis major muscle, extending to the user's clavicle and into the armpit.

Figure 1B:
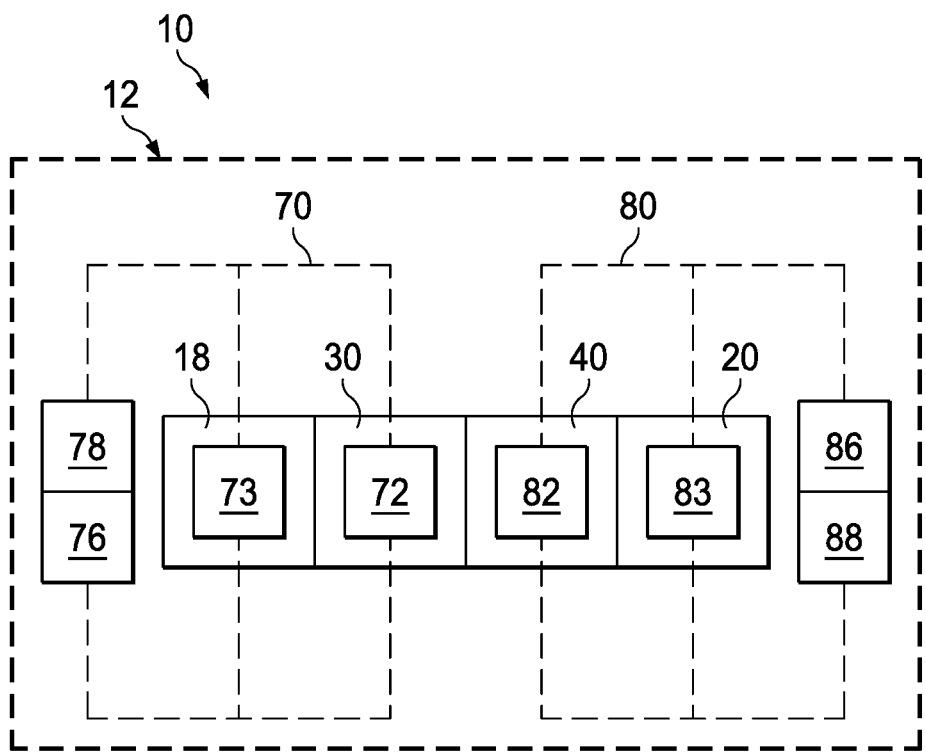
FIG. 1B is a functional block diagram of an embodiment of a therapeutic bra that can provide heat therapy in accordance with this specification.
Figure 1C:
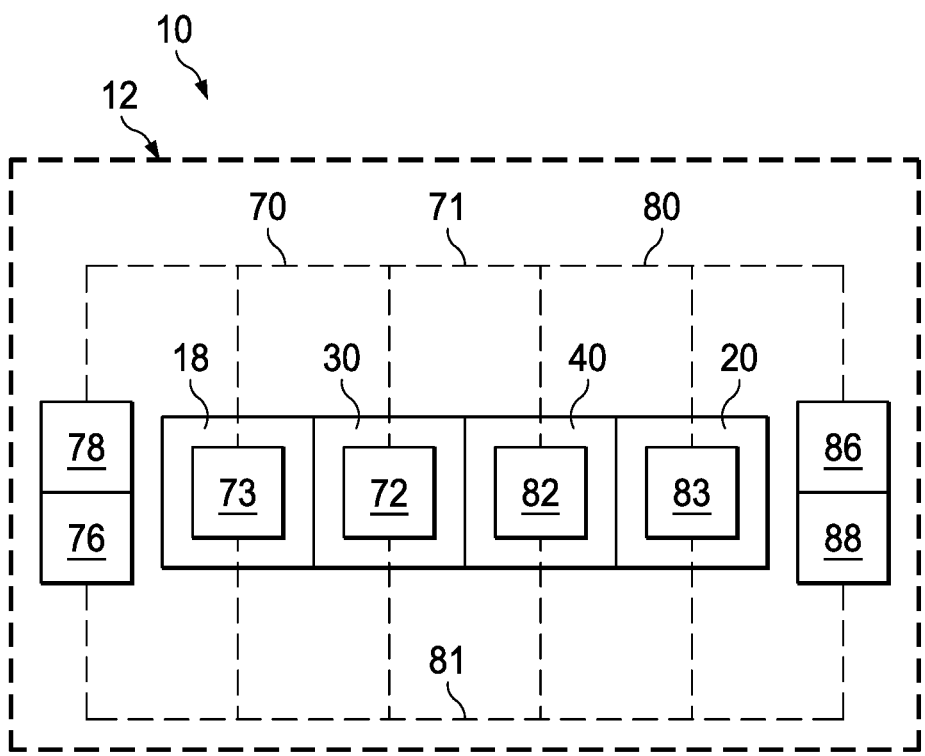
FIG. 1C is a functional block diagram of an embodiment of a therapeutic bra that can provide heat therapy in accordance with this specification.

In some embodiments, as shown in FIG. 1A, the therapeutic bra 10 may comprise a body portion 12 having a first cup 30 coupled to a second cup 40, including at least one of a first heating apparatus and a second heating apparatus. The first heating apparatus comprising at least one first heating loop 72 disposed in the first cup 30, at least one power source 76, and at least one controller 78. The second heating apparatus comprising at least one second heating loop 82 disposed in the second cup, at least one power source 86, and at least one controller 88. The first and second heating apparatuses, as shown in in FIGS. 1A, 1B, 1C, are configured to operate the first and/or second heating loops 72, 82 to heat the first and second cups 30, 40, respectively, simultaneously or independently. In some embodiments described herein, the first and second heating apparatuses are each associated with a first and/or second flap, respectively.

A "cup" is meant to be construed broadly to mean that portion of the bra configured to overlay a user's breasts when worn (e.g., a breast cup). A cup may be structured or unstructured, molded or unmolded, and/or single-layer or multi-layer.

In an embodiment, the therapeutic bra may comprise at least one electric circuit (e.g., a first electric circuit 70 and/or a second electrical circuit 80). In some embodiments, a first electric circuit 70 may comprise the first power source 76 in electric connection with the first heating loop 72, and the controller 78 configured to selectively operate the first heating loop. In some embodiments, a second electric circuit 80 may comprise the second power source 86 in electric connection with the second heating loop 82, and the controller 88 configured to selectively operate the second heating loop 82.

A "heating loop," in this context, broadly includes any electrically conductive fiber that converts electrical energy into heat, such as a nichrome resistance wire, a kanthal wire, a cupronickel alloy wire, a molybdenum disilicide wire, a positive temperature coefficient ceramic element (e.g., a ceramic material having a positive temperature coefficient of resistance, also referred to as a PTC ceramic element), and a conductive thread. In some embodiments, the heating loop be a carbon nanotube coated thread; for example, Electro-Yarn manufactured distributed by Global Signature of San Jose, Calif. The heating loop is comprised of an electrically conductive fiber is malleable with a low profile. In some embodiments, the electrically conductive fiber has a diameter and/or density substantially similar to a nonconductive fiber (non-coated thread, cotton, spandex, polyester, nylon, etc.) such that the user cannot feel a raised portion of the electrically conductive fiber in the textile. In a particular example, the electrically conductive fiber has a density from about 200 dtex to about 500 dtex, and, in other examples, the density is from about 240 dtex to about 400 dtex.

A "power source," is generally known in the art as any component that supplied power to at least one electric load, for example, a battery. In some embodiments, the power source may comprise of a rechargeable lithium polymer li-po battery.

In some embodiments, as shown in FIG. 1A, the body portion 12 may further comprise a first side 18 coupled to the first cup 30, and a second side 20 coupled to the second cup 40. At least a portion of the first heating loop 72 may be further disposed in the first side 18. At least a portion of the second heating loop 82 may be further disposed in the second side 20. The first controller 78 may be in electric connection with the first power source 76, the first heating loop 72, and the second heating loop 82. The first controller 78 may be configured to operate the first heating loop 72 to heat the first cup 30 and the first side 18, and the second heating loop 82 to heat the second cup 40 and the second side 20, simultaneously and/or independently.

In an embodiment, as shown in FIG. 1B, the therapeutic bra 10 may further comprise a second power source 86 and a second controller 88. The first controller 78 may be in electric connection with the first power source 76 and the first heating loop 72, and the second controller 88 may be in electric connection with the second power source 86 and the second heating loop 82. The first controller 78 and the second controller 88 may be configured to selectively operate the first heating loop 72 to heat the first cup 30 and the second heating loop 82 to heat the second cup 40, simultaneously or independently.

In another exemplary embodiment, the therapeutic bra 10 may further comprise a third heating loop 73 disposed in the first side 18 and a fourth heating loop 83 disposed in the second side 20. The first controller 78 may be configured to selectively operate the first heating loop 72 to heat the first cup 30 and the third heating loop 73 to heat the first side 18, simultaneously or independently. The second controller 88 may be configured to selectively operate the second heating loop 82 to heat the second cup 40 and the fourth heating loop 83 to heat the second side 20, simultaneously or independently.

In an embodiment, the therapeutic bra may comprise at least one electric circuit (e.g., a first electric circuit 70 and/or a second electrical circuit 80). In some embodiments, a first electric circuit 70 may comprise the first power source 76 in electric connection with the first heating loop 72, third heating loop 73, and the controller 78 configured to selectively operate the first heating loop. In some embodiments, a second electric circuit 80 may comprise the second power source 86 in electric connection with the second heating loop 82, fourth heating loop 83, and the controller 88 configured to selectively operate the second heating loop 82.

Referring now to FIG. 1C, the therapeutic bra 10 may comprise, a first electric circuit 70, which may comprise the first power source 76 in electric connection with the first heating loop 72, and the controller 78 configured to selectively operate the first heating loop. In some embodiments, a second electric circuit 80 may comprise the second power source 86 in electric connection with the second heating loop 82, and the controller 88 configured to selectively operate the second heating loop 82. A first connecting portion 71 and/or a second connecting portion 81 to electrically connect the first and second electric circuits 70, 80. In an embodiment, the therapeutic bra 10 includes both the first and second circuits connected via first and/or second connecting portions 70, 80 as described herein which advantageously can provide at least one of the following benefits: improved heat output, increased heat output, and a redundant circuit operable if either the first or second circuit 70, 80 malfunctions.

Figure 1D:
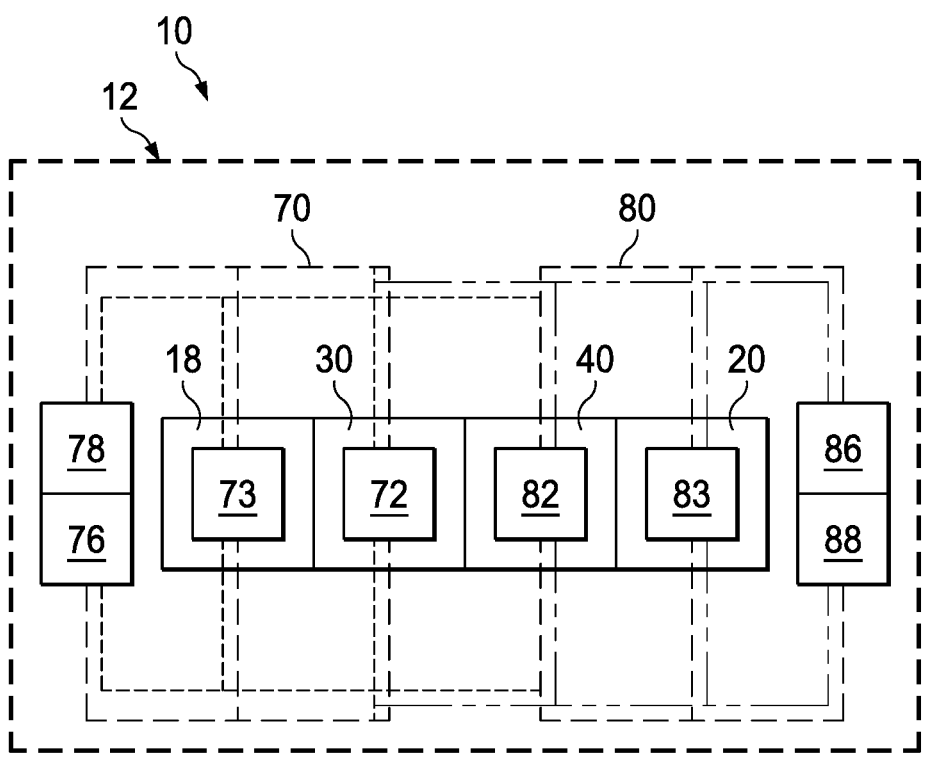
FIG. 1D is a functional block diagram of an embodiment of a therapeutic bra that can provide heat therapy in accordance with this specification.

Referring now to FIG. 1D, the therapeutic bra 10 may comprise at least one electric circuit (e.g., a first electric circuit 70 and/or a second electric circuit 80). In some embodiments, a first electric circuit 70 may comprise a first power source 76 in electric connection with the first heating loop 72, the second heating loop 82, and the controller 78 configured to selectively operate the first heating loop 72 and the second heating loop 82, simultaneously or independently. In some embodiments, the first electrical circuit 70 further includes the third and fourth heating loops 73, 83. In some embodiments, a second electric circuit 80 may comprise a first power source 76 in electric connection with the first heating loop 72, the second heating loop 82, and the controller 78 configured to selectively operate the first heating loop 72 and the second heating loop 82, simultaneously or independently. In some embodiments, the second circuit 80 further includes the third and fourth heating loops 73, 83. In an embodiment, the therapeutic bra 10 includes both the first and second circuits as described herein which advantageously can provide at least one of the following benefits: improved heat output, increased heat output, and a redundant circuit operable if either the first or second circuit 70, 80 malfunctions.

In an exemplary embodiment, the therapeutic bra 10 may comprise at least one electric circuit (e.g., a first electric circuit 70). In some embodiments, a first electric circuit 70 may comprise a first power source 76 in electric connection with the first heating loop 72 (e.g., there is no second heating loop 82), and the controller 78 configured to selectively operate the first heating loop 72 associated with the body (e.g., the first cup 30, the first side 18, the front 14, the second cup 40, the second side 20), a first flap as described herein, a second flap as described herein, and combinations thereof. In some embodiments, the first heating loop 72 is configured as one continuous heating loop through the front 14; the sides 18, 20; any flaps as described herein; and any combinations thereof.

Figure 2A:
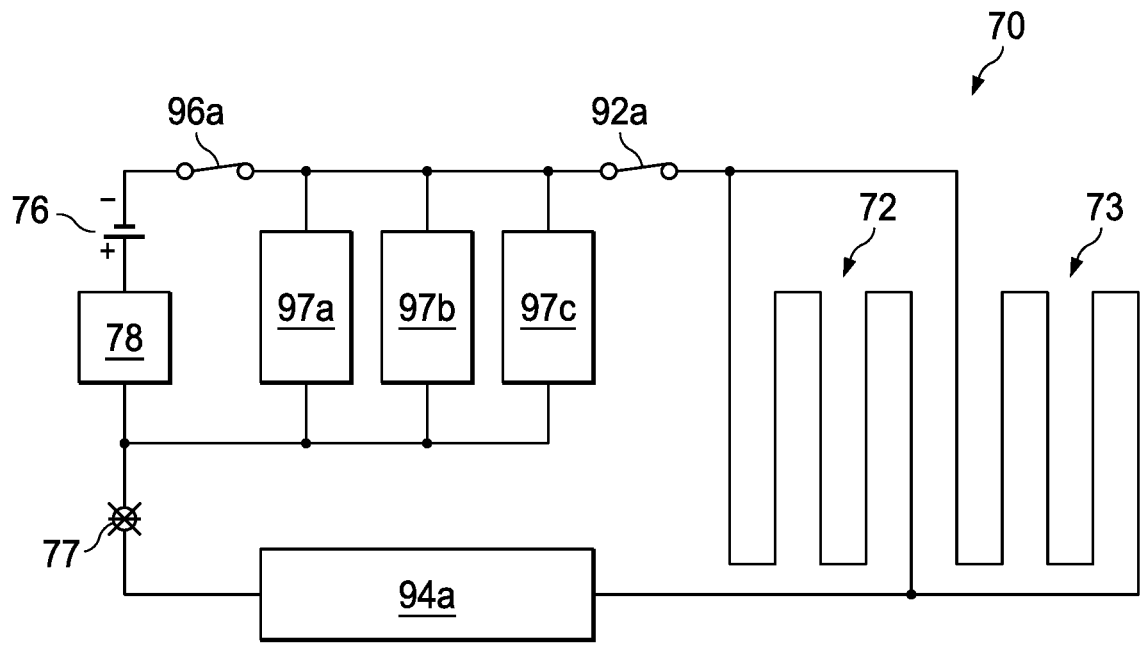
FIG. 2A is a schematic diagram of an exemplary embodiment of an electric circuit associated with the therapeutic bra described herein.

Referring now to FIG. 2A, in some embodiments of therapeutic bra 10, electric circuit 70 includes a second heating loop 72, and may also comprise a third heating loop 73, in electric connection with the controller 78, wherein the controller 78 is configured to selectively operate the first heating loop 72 and the third heating loop 73, simultaneously or independently.

Figure 2B:
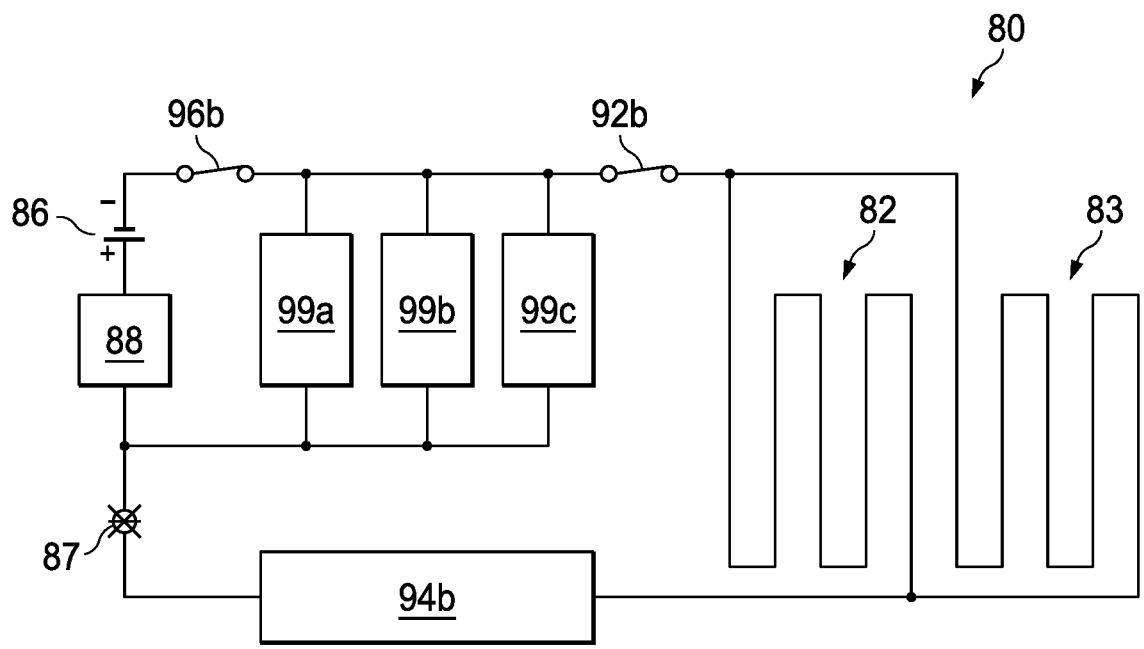
FIG. 2B is a schematic diagram of an exemplary embodiment of an electric circuit associated with the therapeutic bra described herein.

Referring now to FIG. 2B, the electric circuit 80 includes a third heating loop 82, and may also comprise a fourth heating loop 83, in electric connection with the controller 88, wherein the controller 88 is configured to selectively operate the second heating loop 82 and the fourth heating loop 83, simultaneously or independently.

In an embodiment, shown in FIGS. 2A-2B, first and/or second electric circuit 70, 80 may further comprise at least one thermal sensor disposed in proximity to each heating loop. For example, first thermal sensor 94a disposed in proximity to the first heating loop 72 and second thermal sensor 94b disposed in proximity to the second heating loop 82. The first thermal sensor 94a may be electrically connected to the first controller 78 and the second thermal sensor 94b may be electrically connected to the second controller 88. A person of ordinary skill in the art will recognize that the above-mentioned components can have different arrangements in other embodiments.

Sensors are generally known in the art as any apparatus operable to detect or measure a physical phenomenon or property that is detected or measured. For example, first thermal sensor 94a and second thermal sensor 94b may be configured to measure the temperature of first heating loop 72 and second heating loop 82, respectively. Preferably, the signals from the first thermal sensor 94a and the second thermal sensor 94b are suitable as an input to signal the first controller 78 and the second controller 88, respectively. Typically, the signal is an electric signal, but may be represented in other forms, such as an optical signal.

The controller may be further configured to receive and process data from one or more sensors, such as first thermal sensor 94a and second thermal sensor 94b. In such embodiments, the first thermal sensor 94a can transmit a first signal to the controller 78 if a sensed temperature exceeds a desired temperature that correlates to a maximum intensity level for the first heating loop 72. Likewise, the second thermal sensor 94b can transmit a first signal to the controller 88 if a sensed temperature exceeds a desired temperature that correlates to a maximum intensity level for the second heating loop 82. In response to the first signal, the first controller 78 and the second controller 88 may transmit a second signal to the first power source 76 and the second power source 86, respectively. In response to the second signal, the first power source 76 and the second power source 86 may cause the current that is applied to the first heating loop 72 and the second heating loop 82. In other embodiments, the first and/or second thermal sensor 94a, 94b may sense and transmit one or more signals in response to a range of temperatures.

In some embodiments, a thermal sensor may be a programmable SOT switch, such as first thermal switch 92a and second thermal switch 92b.

The first electric circuit 70 and the second electric circuit 80 may further comprise a time switch.

A "time switch" in this context broadly refers to a timer that operates an electric switch to open after a predetermined interval of time. In some embodiments the time switch may be programmable.

Referring to FIGS. 2A and 2B, the first electric circuit 70 may further comprise a first time switch 96a and second electric circuit 80 may further comprise a second time switch 96b. The first time switch 96a may be configured to turn off the first heating loop 72 after a predetermined interval of time and the second time switch 96b may be configured to turn off the second heating loop 82 after a predetermined interval of time.

In some embodiments, the first electric circuit 70 and the second electric circuit 80 may further include an indicator light, such as first LED 77 and second LED 87, as seen in FIG. 2A and FIG. 2B, respectively. The first LED 77 and the second LED 87 operate at an illumination intensity level that is responsive to a current applied to the first LED 77 and the second LED 87. The minimal intensity level may be dictated by federal regulations or recommended by regulatory agencies and/or industry standards.

In other embodiments, the first electric circuit 70 and/or the second electric circuit 80 may further comprise a plurality of vibrating devices 97. The term "vibrating device," in this context broadly refers to an electrical and/or mechanical device that generate and/or apply vibrations. In some embodiments, the vibrating device applies ultrasonic vibrations. Vibration means a change in a force vector (i.e., a change in direction or magnitude) of a rotating mass that the user perceives as a vibration (e.g., an oscillating force).

The plurality of vibrating devices 97 may be disposed in the first cup 30, the second cup 40, the first side 18, the second side 20, or a combination thereof. As seen in FIGS. 2A-2B, the plurality of vibrating devices 97 comprise first vibrating device 97a, second vibrating device 97b, third vibrating device 97c, fourth vibrating device 97d, fifth vibrating device 97e, and sixth vibrating device 97f. During operation, physical vibration is externally applied to the user by at least one of the vibrating devices 97a, 97b, 97c, 97d, and/or 97e. In some embodiments, the plurality of vibrating devices 97 externally apply physical vibration to the user at the same time continuously. In some embodiments, the plurality of vibrating devices 97 externally apply physical vibration to the user sequentially by the vibrating devices 97a, 97b, 97c, 97d, 97e; for example, the first vibrating device 97a applies vibration first, the second vibrating device 97b applies vibration second, the third vibrating device 97c applies vibration third, etc. It will be understood by those skilled in the art that the actual sequence could be varied to treat different areas of the user.

In an illustrative embodiment, the first, second, and third vibrating devices 97a, 97b, and 97c, may be associated with the first electric circuit 70 and may be in electric connection with the first power source 76 and the first controller 78. The first controller 78 may be further configured to operate the first, second, and third vibrating devices 97a, 97b, and 97c, simultaneously or independently. Likewise, the fourth, fifth, and sixth vibrating devices 97d, 97e, and 97f, may be associated with the second electric circuit 80 and may be in electric connection with the second power source 86 and the second controller 88. The second controller 88 may be further configured to operate the fourth, fifth, and sixth vibrating devices 97d, 97e, and 97f, simultaneously or independently.

Figure 3A:
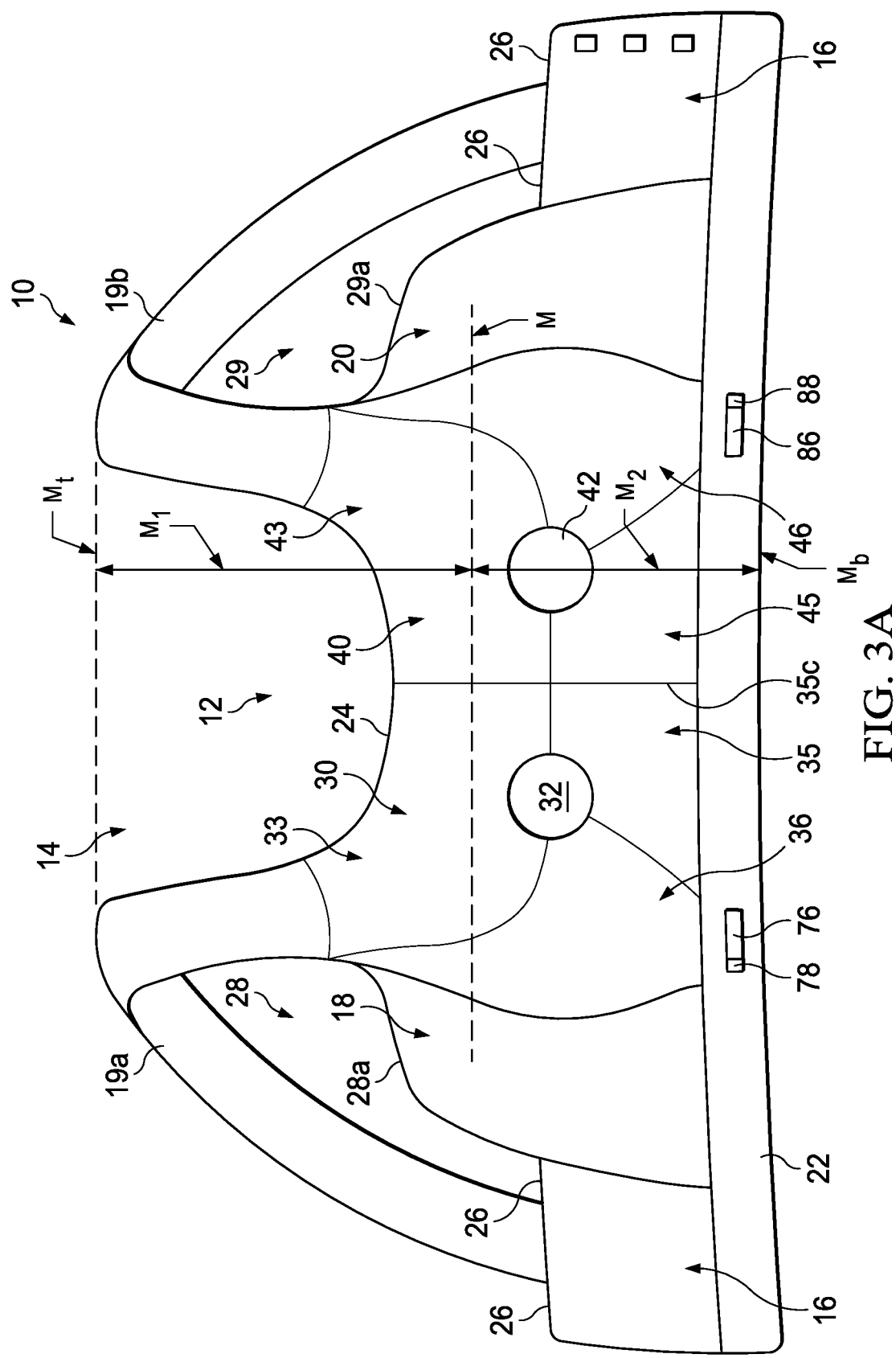
FIG. 3A is a diagram illustrating an exterior view of an exemplary embodiment of the therapeutic bra described herein.

FIG. 3A is a diagram illustrating an exterior view of an example embodiment of a therapeutic bra 10. As seen in FIG. 3A, the body portion 12 of therapeutic bra 10 may be configured to fit around a back and chest of the user and may comprise a front 14, a back 16, the first side 18 coupled to the front 14 and the back 16, and the second side 20 coupled to the back 16 and the front 14. In some embodiments the body portion 12 may further comprise a band 22, a first strap 19a, and a second strap 19b. The first strap 19a and the second strap 19b may be coupled to the front 14 and the back 16 for securing the bra on the shoulders of the user. The straps 19a, 19b are configured to overlay a shoulder area of the user and may have a number of different configurations such as racerback, convertible, standard, and the like. The back 16 is configured to overlay a back upper torso area of the user and may be connected to the front 14 in part through the straps 19a, 19b (e.g., a first strap 19a is connected at the front on the right side of the user, a second strap 19b is connected at the front on the left side of the user).

The front 14 of the body portion 12 can include a first upper portion 33, which is located at a top and adjacent to the strap 19a; a first lower portion 35, which is located at the bottom and adjacent to the band 22, a first side portion 36, which is adjacent to the first side 18. The front 14 of the body portion 12 may further comprise a second upper portion 43, which is located at the top and adjacent to the strap 19b; a second lower portion 45, which is located at the bottom and adjacent to the band 22; and a second side portion 46, which is adjacent to the second side 20.

The optional band 22 is configured to encircle the user's torso at a lower or inferior margin of the body portion 12. The band 22 may be disposed adjacent to the body portion 12 and may extend circumferentially around the back and chest of the user. The band 22 may be integral or separate with the body portion 12.

In some embodiments, the front 14 may comprise the first cup 30 coupled to the second cup 40, and a neckline 24. The first cup 30 may be coupled to the first side 18 and the second cup 40 may be coupled to the second side 20. The first and second cups 30, 40 can each have a dome shape and/or stretchable to a dome shape. The cup 30 can include a first opening 32 centrally located therein between the first upper portion 33, the first lower portion 35, and the first side portion 36. The second opening 42 may be centrally located in the second cup 40 between the second upper portion 43, the second lower portion 45, and the second side portion 46. In some embodiments, the first cup 30 includes a first opening 32 configured to receive a first nipple of a user or a breast pump therethrough. In some embodiments, the second cup 40 includes a second opening 42 configured to receive a second nipple of a user or a breast pump therethrough. The first cup 30 and the second cup 40 may be separated or joined at a center bridge 35c.

The bra 10 includes a latitudinal midline M (see FIG. 3A) that evenly divides the front 14 of bra 10 into a top half $M_1$ having the straps 19a, 19b, and a bottom half $M_2$ having first and second lower portions 35, 45, and/or band 22. The top half $M_1$ includes a topmost point Mt in the respective strap 19a, 19b (e.g., the top of the band at the top of the user's shoulder). The bottom half $M_2$ includes a bottom most point $M_b$ of the band 22 (e.g., the bottom edge) or, in embodiments without a band 22, at the bottom of the first and second lower portions 35, 45. In the exemplary embodiment shown in FIG. 3A, the neckline 24 is substantially aligned with the latitudinal midline M. In other embodiments, having a higher or full coverage neckline the neckline 24 is above the latitudinal midline M. In an exemplary embodiment of a higher neckline 24, the neckline 24 is disposed in the top half $M_2$ of the bra. In some embodiments, the higher neckline 24 may extend to approximately an inch below the user's collarbones so that the front 14 covers the entire breast tissue on the chest of the user. Advantageously, the full coverage and/or higher neckline as described herein provides therapeutic heat and/or vibration to the Spence space of the breast tissue as well as the top two quadrants of the breast that reach the second rib just below the clavicle (during lactation the breast tissue expands to fill these spaces).

In some embodiments, the first power source 76 and the first controller 78 may be disposed on or within the band 22, and/or near or adjacent to the first cup 30 (for example, but not limitation, the first lower portion 35). In other embodiments, the first power source 76 and the first controller 78 may be disposed on or within the first strap 19a, near or adjacent to the first cup 30. In some embodiments, the second power source 86 and the second controller 88 may be disposed on or within the band 22, and/or near or adjacent to the second cup 40 (for example, but not limitation, the second lower portion 45). In other embodiments, the second power source 86 and the second controller 88 may be disposed on or within the second strap 19b, near or adjacent to the second cup 40.

In some embodiments, the first and second straps 19a and 19b may be coupled to form a racerback style bra. In other embodiments, the first and second straps 19a and 19b may be separate. In such embodiments, the first strap 19a may be coupled to the back 16 near or adjacent to the first side 18 and the second strap 19b may be coupled to the back 16 near or adjacent to the second side 20. Alternatively, in some embodiments, the first strap 19a may be coupled to the back 16 near or adjacent to the second side 20 and the second strap 19b may be coupled to the back 16 near or adjacent to the first side 18, so that the straps 19a and 19b cross at the back of the user. In some embodiments, the length of the first strap 19a and the second strap 19b may be adjustable.

The back 16 may comprise a backline 26. The first side 18 may comprise a first underarm line 28a and the second side 20 may comprise a second underarm line 29a. In some embodiments the first and second underarm lines 28a, 29a extend to the creases in the user's first and second underarms to provide high coverage of the breast tissue in this area, as shown in FIG. 4C. Advantageously, the full coverage of bra 10 can extend in some embodiments to first and second underarm lines 28a, 29a to provide therapeutic heat and/or vibration to the Spence space of the breast tissue as well as the top two quadrants of the breast that reach the second rib just below the clavicle (during lactation the breast tissue expands to fill these spaces).

The therapeutic bra 10 may further comprise a first arm hole 28 and a second arm hole 29. The first arm hole 28 is defined by the first strap 19a, the first underarm line 28a, and the backline 26. The second arm hole is defined by the second strap 19b, the second underarm line 28b, and the backline 26. In some embodiments wherein the first and second straps 19a, 19b cross at the back of the user, the first arm hole 28 is defined by the first strap 19a at a top portion and the second strap 19b at a bottom portion and the second arm hole 29 is defined by the first strap 19a at a bottom portion and the second strap 19b at a top portion.

Figure 3B:
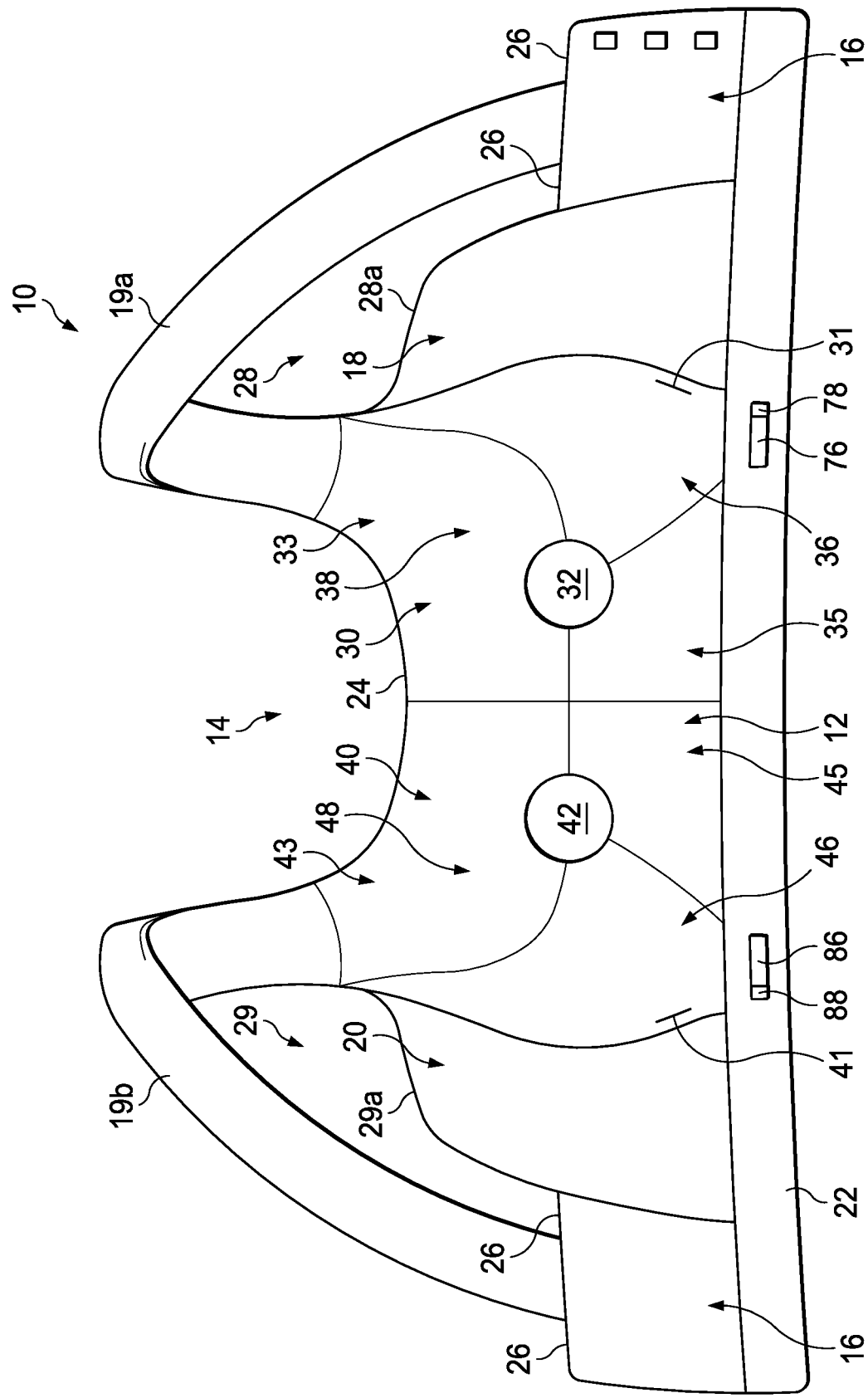
FIG. 3B is a diagram illustrating an interior view of an exemplary embodiment of the therapeutic bra described herein.

FIG. 3B is a diagram illustrating an interior view of an example embodiment of the therapeutic bra of FIG. 3A. In this context, "interior" refers to the side of the therapeutic bra 10 that when worn, is in contact with the user. In some embodiments, the interior of the first cup 30 and the second cup 40 of therapeutic bra 10 may comprise molded cups. For example, as seen in FIG. 3B, the interior of first cup 30 may comprise a first interior convex curved surface 38 and the interior of second cup 40 may comprise a second interior convex curved shaped surface 48 (e.g., convex curve means a curve bending outward from the first/second side portions 36, 46 and/or the first/second lower portions 35, 45. In this context, a "molded cup" refers broadly to a structured breast support as known in the art. In general, molded cups form a convex curve shape and may be made in various sizes to accommodate the breast tissue of the user.

In some embodiments, body portion 12 may comprise a first underwire slit 31 disposed on the first interior convex curved surface 38 of the first cup 30 and a second underwire slit 41 disposed on the second interior convex curved surface 48 of the second cup 40. The first underwire slit 31 and the second underwire slit 41 allow the user to insert a removable plastic underwire for added support.

Figure 4A:
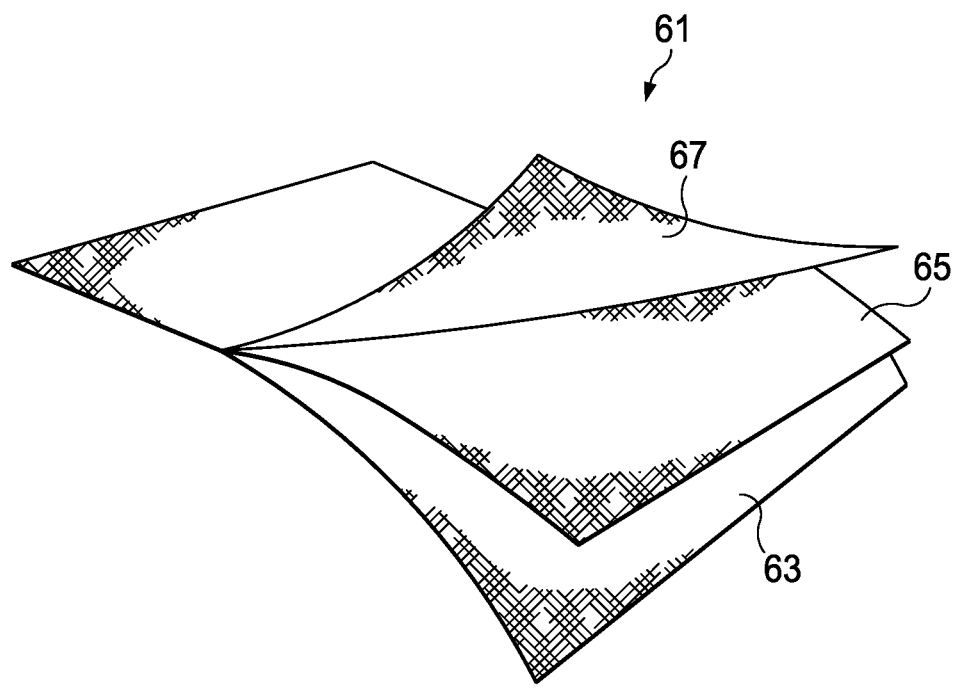
FIG. 4A is an exploded view of an exemplary embodiment of a textile associated with a therapeutic bra that can provide heat therapy in accordance with this specification.

Referring now to FIG. 4A, in some embodiments, the body portion 12 and/or at least one flap 50 of therapeutic bra 10 may comprise a textile 61. In an embodiment, the textile 61 is a multi-layer textile. In other embodiments, the textile 61 is a single layer. The textile 61 may comprise knit or woven fibers as generally known in the art; for example, the textile 61 may comprise a non-conducting textile such as cotton, polyester, spandex, nylon, silk, or a combination thereof. In some embodiments, the textile 61 may comprise an inner layer 63 that contacts the skin of the user, an outer layer 67, and a center layer 65 disposed between the inner layer 63 and the outer layer 67.

In some embodiments of the therapeutic bra 10, the first heating loop 72 and the second heating loop 82 may be disposed between the center layer 65 and the inner layer 63. In other embodiments of the therapeutic bra 10, the first heating loop 72 and the second heating loop may be disposed between the center layer 65 and the outer layer 67.

Figure 4B:
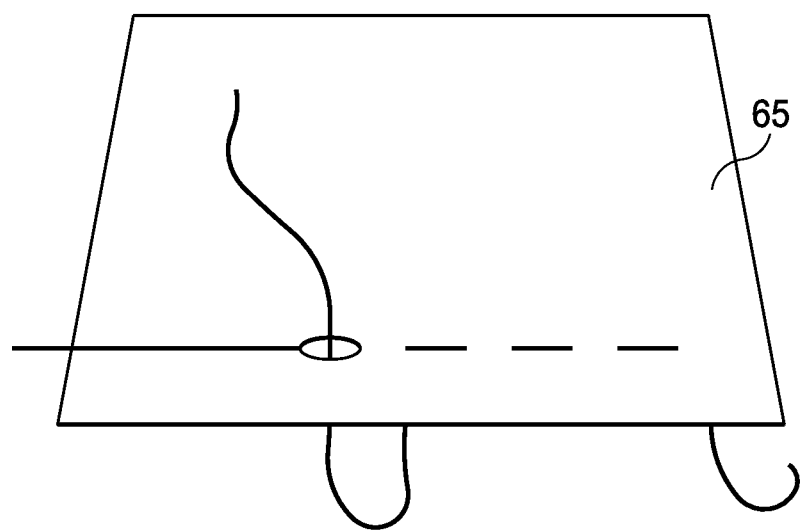
FIG. 4B is a diagram illustrating the disposition of a heating loop with respect to the textile of FIG. 4A.
Figure 4C:
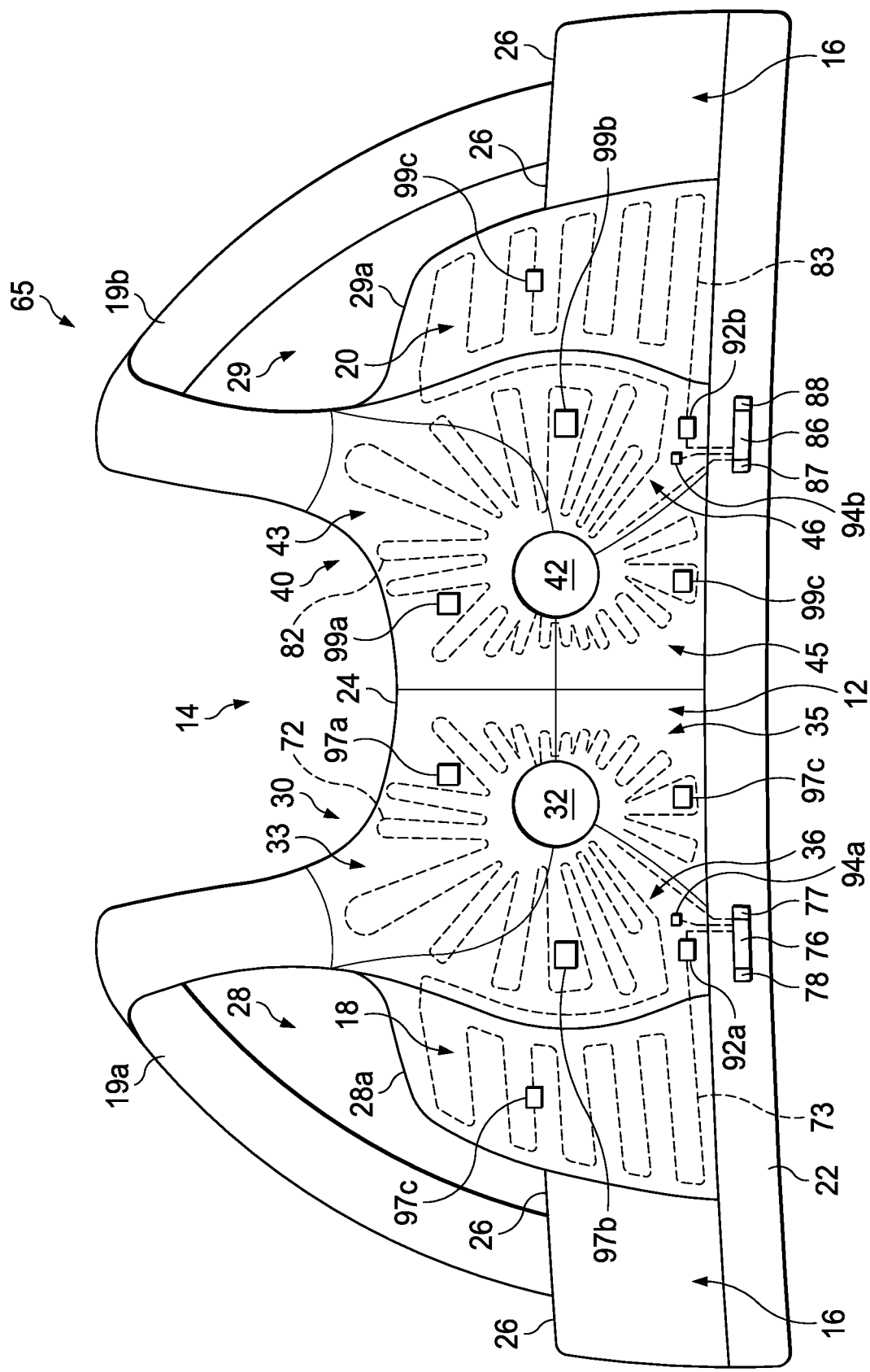
FIG. 4C is a diagram illustrating the center layer of an example embodiment of the therapeutic bra of FIG. 1.

In some embodiments, the first heating loop 72 and the second heating loop 82 are each comprised of a thin, flexible, continuous, length of a heat conductive material that may be stitched through a layer of the textile (e.g., a layer 63, 65, and/or 67) (e.g., using a straight stitch). In some embodiments, the first and second heating loops 72, 82 are interwoven, embedded, and/or bonded (via adhesive) to a layer (e.g., a layer 63, 65, and/or 67) of the textile. In some embodiments, the thin, flexible, length of the electrically conductive fiber may have a low profile having at least one of the following: a circular cross section and a rectangular cross section (e.g., the heating loop 72 has a low profile that is comfortable for the user). For example, FIG. 4B shows first heating loop 72 interwoven through center layer 65. The first and second heating loops 82 do not extend to the back 16 of the therapeutic bra 10 (e.g., it would be prohibitive to use energy to heat the back of the user since the therapeutic bra 10 is designed to provide heat and vibration therapy for conditions related to lactation).

FIG. 4C is a diagram illustrating the center layer 65 of an example embodiment of the therapeutic bra 10. As seen in FIG. 4C, the first heating loop 72 may be interwoven through the center layer 65 of the band 22 and the first cup 30, and the second heating loop 82 may be interwoven through the center layer 65 of the band 22 and the second cup 40. The third heating loop 73 may be interwoven through the first side 18 and the band 22, and the fourth heating loop 83 may be interwoven through the second side 20 and the band 22. In some embodiments, the third heating loop 73 is operably connected to a third heating device 97c. In an embodiment, the fourth heating loop 83 is operably connected to a sixth heating device 99c.

Figure 8A:
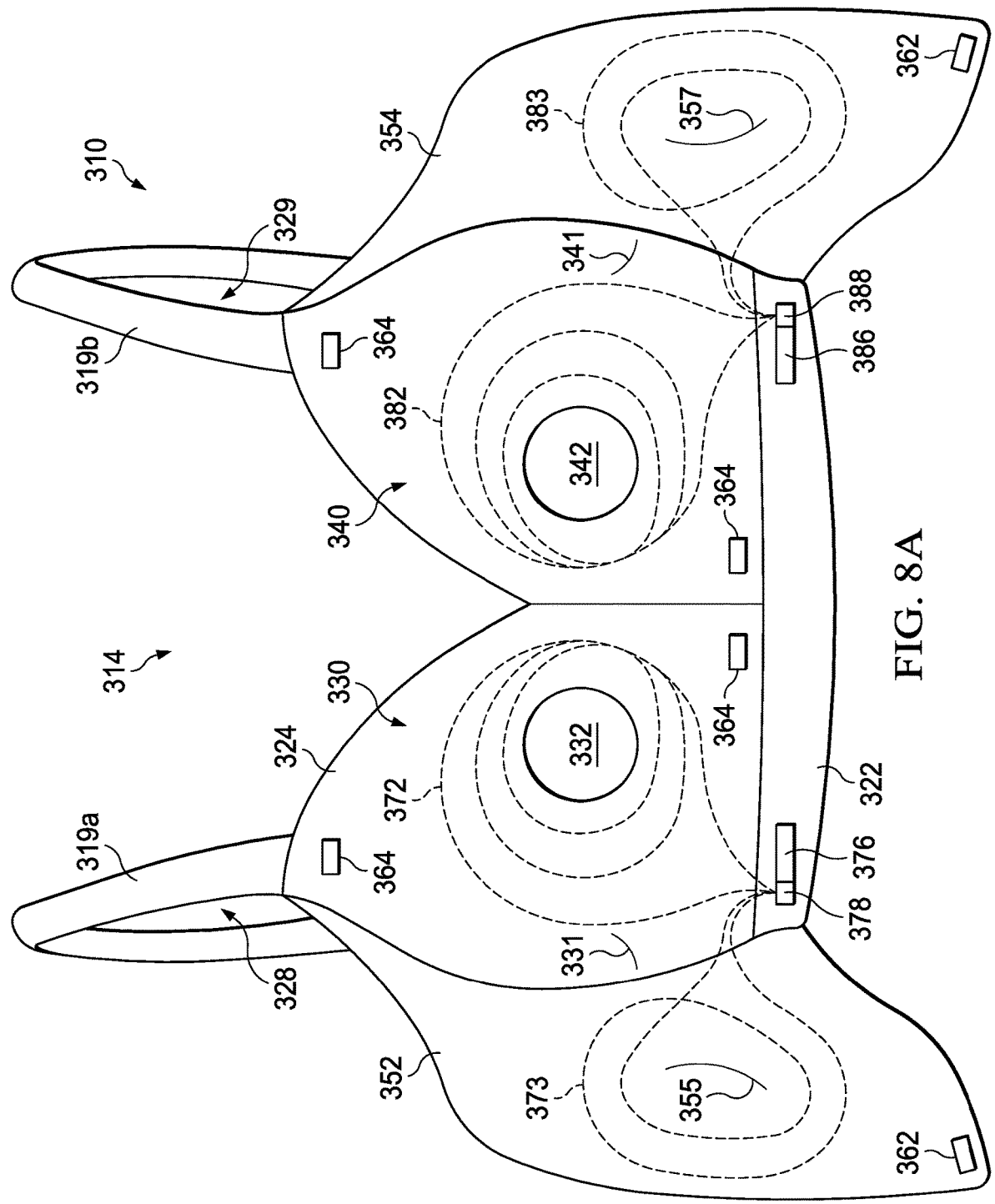
Figure 11A:
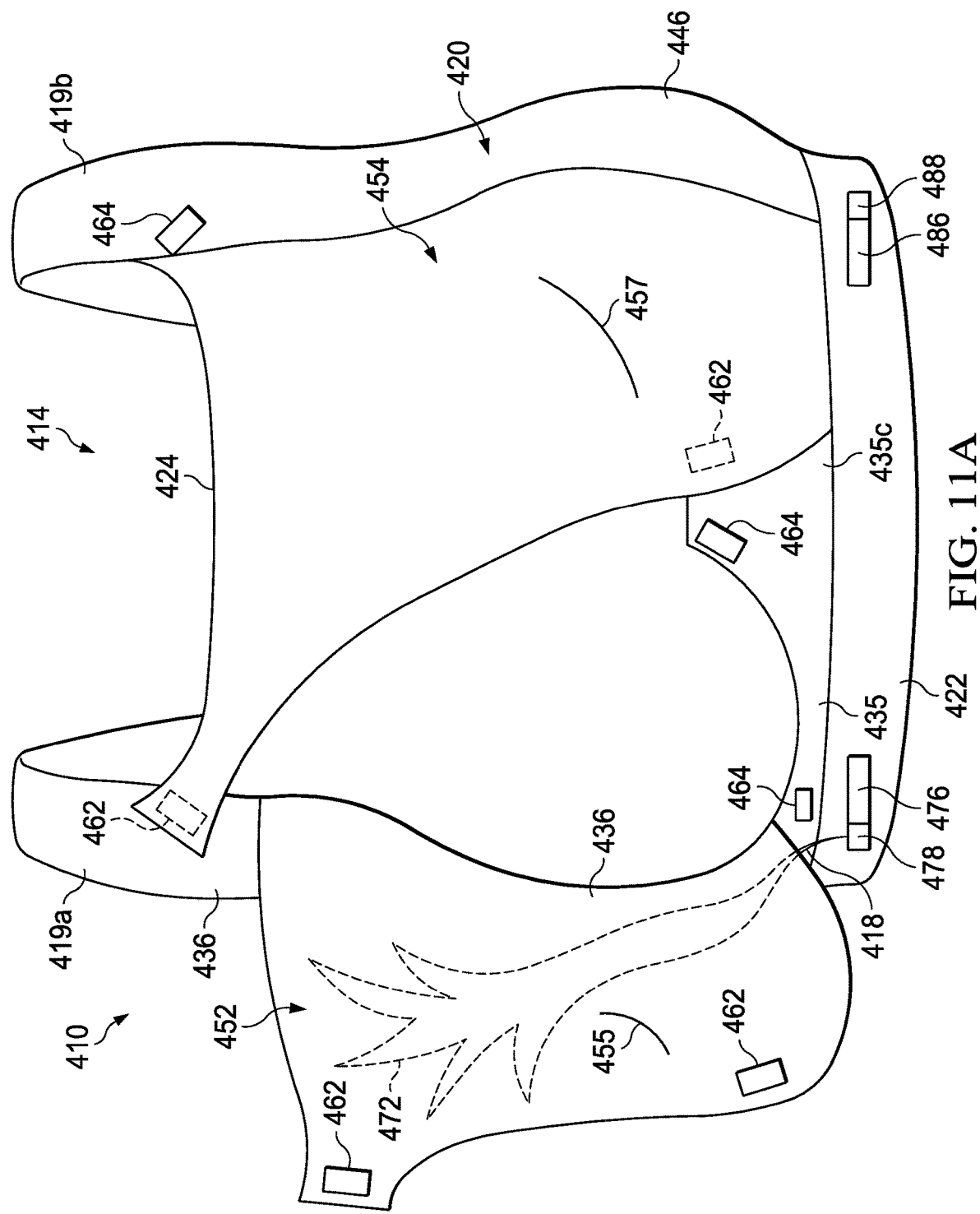
FIG. 11A is a diagram illustrating exemplary features of another embodiment of a therapeutic bra.
Figure 11B:
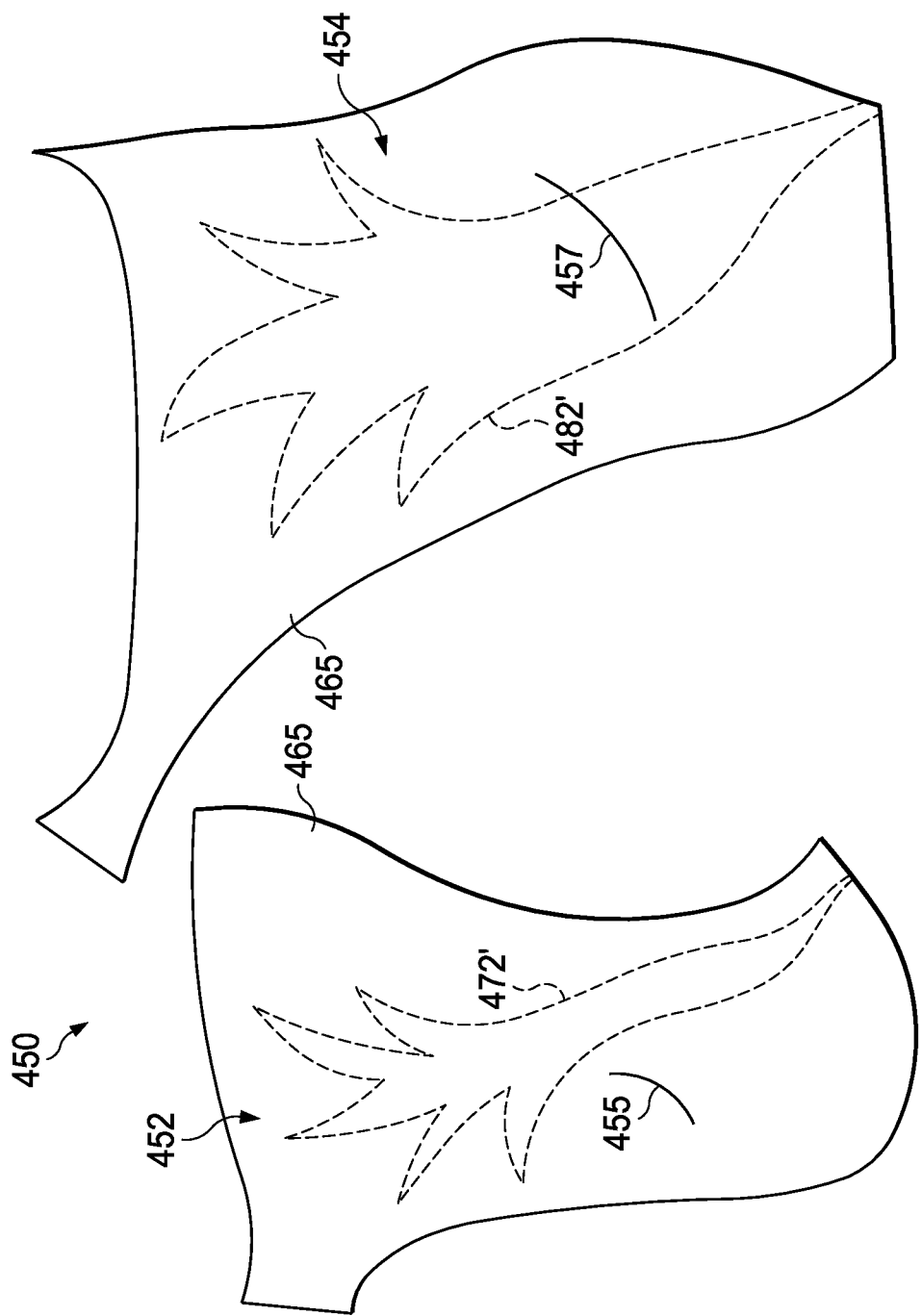
FIG. 11B is a diagram illustrating an internal view of the center layer of the flaps of FIG. 11A.

The first heating loop 72 and/or the second heating loop 82 may be interwoven through the center layer 65 to define a heating pattern. The heating pattern can be a heating loop as described herein (e.g., first and/or second heating loop 72, 82) configured to heat the breast tissue of the user. In an embodiment, the heating pattern is a heating loop including hairpin curves in a radial pattern; for example, as seen in FIG. 4C, the first heating loop 72 may be interwoven through the center layer 65 of the first cup 30 to form hairpin curves in a radial pattern and circumferentially around the first opening 32 and extending toward the edges of the first cup 30. In some embodiments, the heating pattern includes a curved portion to complement a curvature of the user's breast tissue; for example, but not limitation, the heating pattern includes a heating loop positioned concentrically around the first opening 32 and/or the second opening 42, respectively. In some embodiments, the heating pattern is a heating loop including a zigzag portion (radial pattern, FIG. 4C); a connected linear portion, as shown in third and fourth heating loops 73, 83; conjoined substantially concentric circles, as shown in FIGS. 8A and 8C; conjoined substantially nonconcentric circles; and an irregular path portion (FIGS. 11A-11B).

In some embodiments, the first heating loop 72, the second heating loop 82, the third heating loop 73, the fourth heating loop 83, or a combination thereof, may be interwoven through substantially all of the center layer 65 of the first cup 30, the second cup 40, the first side 18, and the second side 20. Advantageously, the therapeutic bra 10 provides at least one of the following benefits to the user: improved milk flow, improved milk quantity (e.g., as much as 30% more); prevents blockages in breast tissue; ducts in the breast tissue of the wear expand when heat is applied thereto, which permits the flow of milk; prevents and helps breast engorgement; stimulates the ducts in the breast tissue; assists with weaning (e.g., permitting flow even with reduced quantity); reduces blocked ducts; reduces milk blebs (e.g., a painful pore infection); reduces pain during pumping, nursing, and weaning; and prevents need for pain medicine. Moreover, the therapeutic bra 10 is designed for the comfort of the user so the bra 10 can be worn all day to work, workout, etc. (e.g., not just when performing lactation activities). The therapeutic bra 10 is configured such that the heating loops are not felt by the user and do not show through clothing (e.g., can be worn under clothes).

In some embodiments of the therapeutic bra 10, the plurality of vibrating devices 97 may be disposed in the center layer 65 of the body portion 12 and may be in electric connection with either the first power source 76 and the first controller 78, or the second power source 86 and the second controller 88. The plurality of vibrating devices 97 may be disposed in the first cup 30, the second cup 40, the first side 18, the second side 20, a first cup, a second cup, or a combination thereof.

As depicted in FIG. 4C, the first vibrating device 97a may be disposed in the center layer 65 of the first upper portion 33, the second vibrating device 97b may be disposed in the center layer 65 of the first side portion 36, the third vibrating device 97c may be disposed in the center layer 65 of the first lower portion 35. The fourth vibrating device 97d may be disposed in the center layer 65 of the second upper portion 43, the fifth vibrating device 97e may be disposed in the center layer 65 of the second side portion 36, and the sixth vibrating device 97f may be disposed in the center layer 65 of the second lower portion 45. There are advantages of applying heat via the heating loops described herein as well as providing vibration using the therapeutic bra 10 including at least one of the following: additional stimulation for blocked ducts, which losses the blockage, as well as pumping and nursing; and assists with inducing lactation (e.g., at the beginning of milk production, when milk "comes in").

Figure 5A:
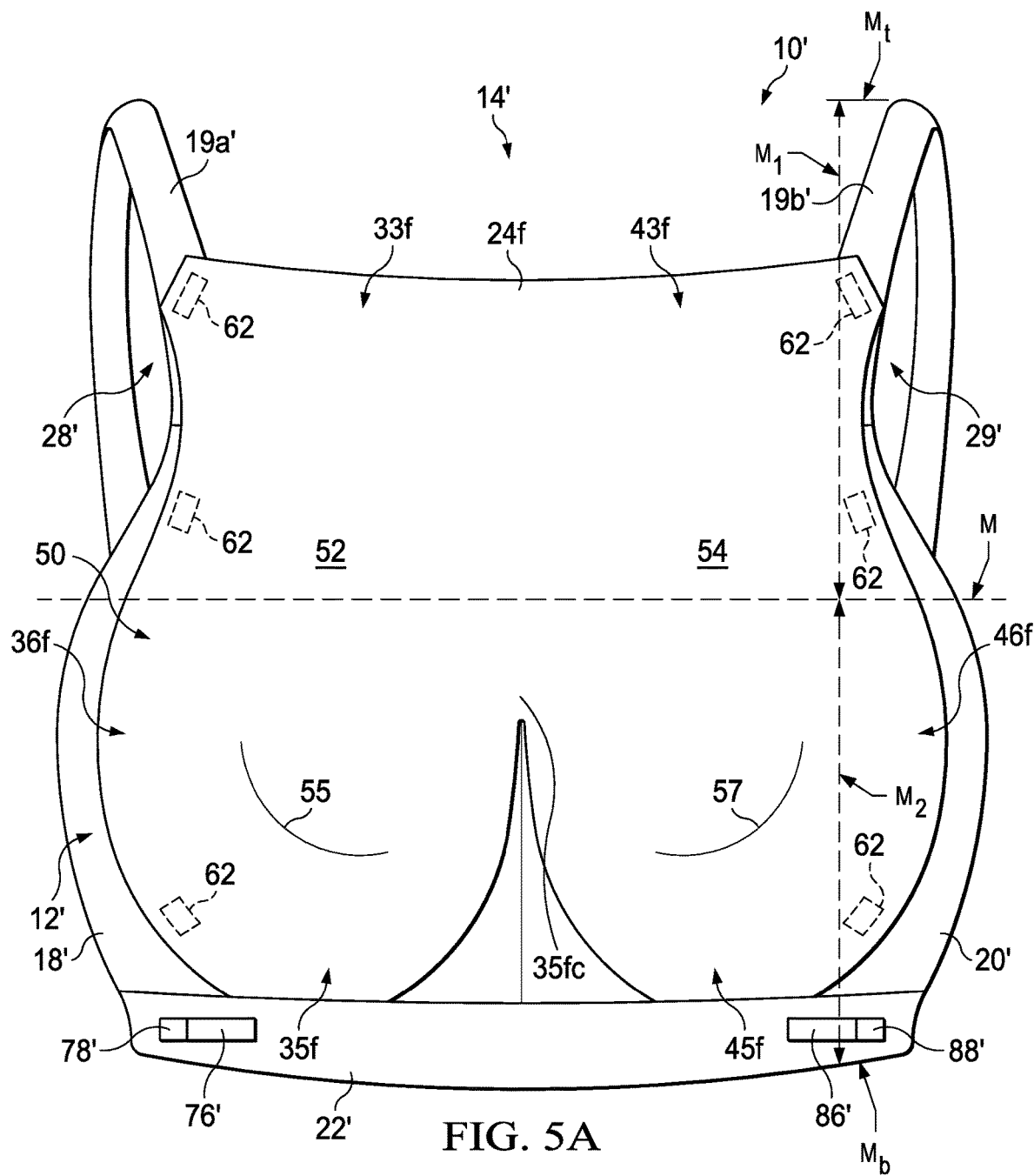
FIGS. 5A-5B are diagrams illustrating an exemplary embodiment of a therapeutic bra.
Figure 5B:
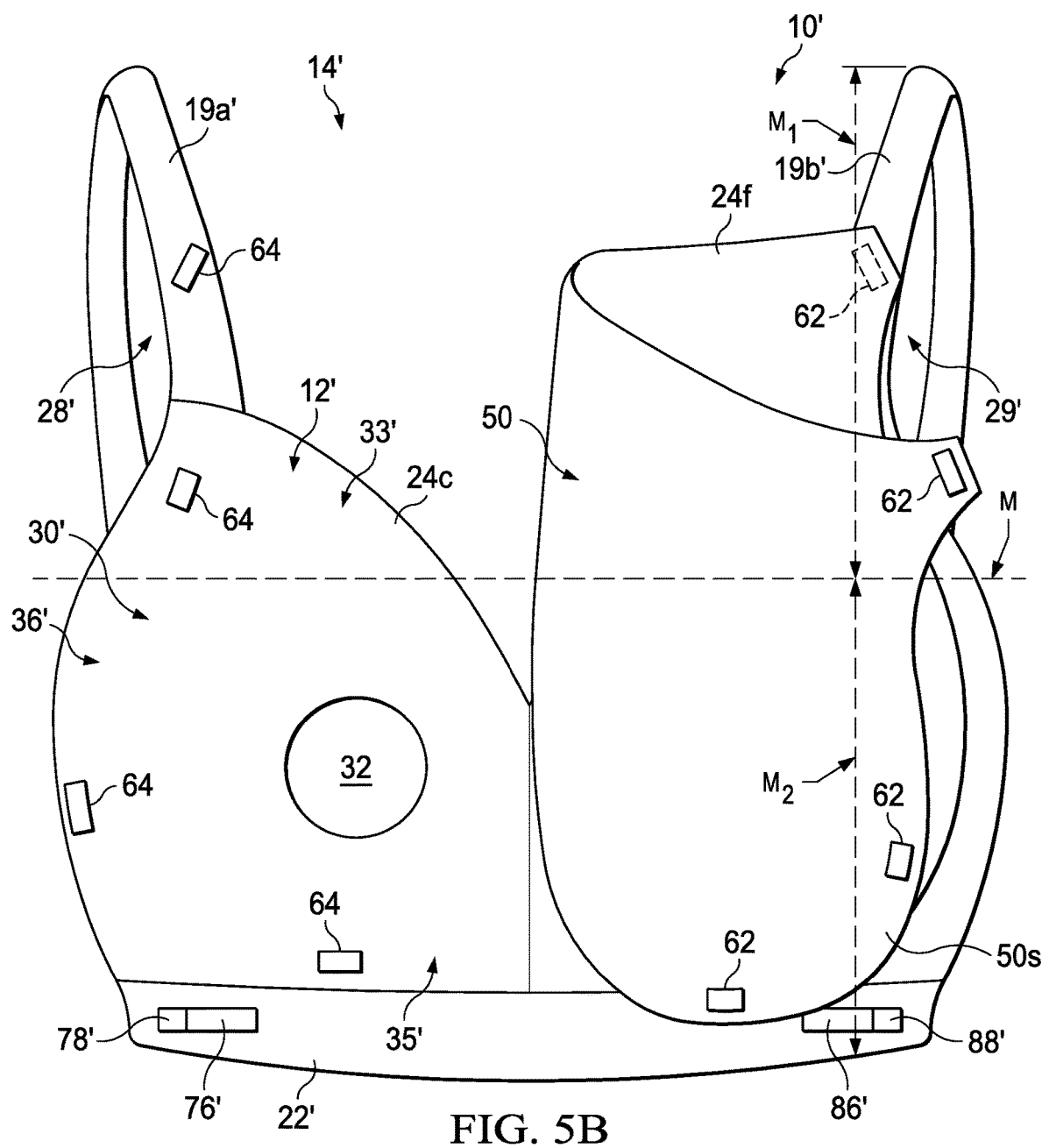
Figure 5C:
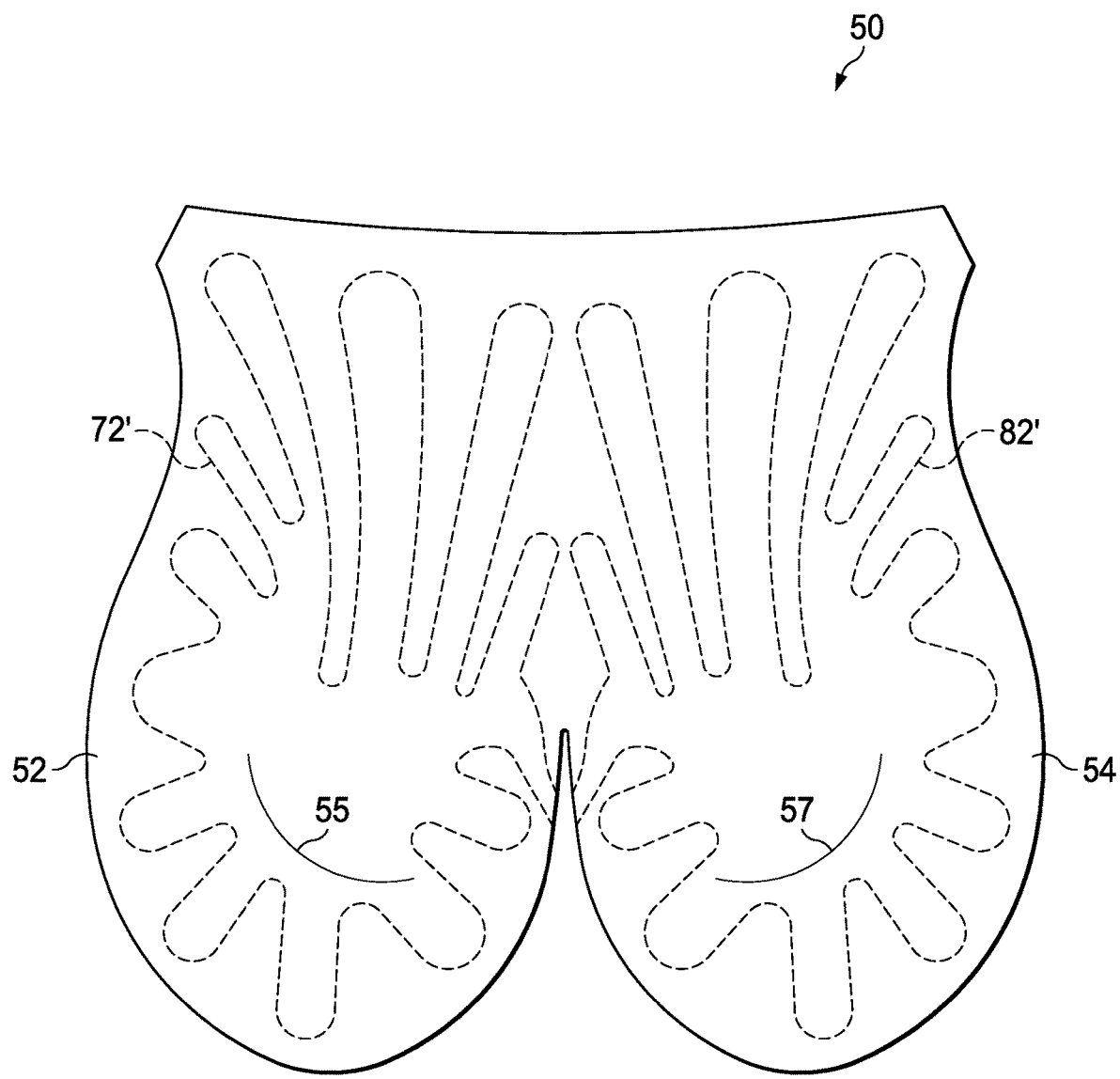
FIG. 5C is a diagram illustrating the center layer of the flap of FIGS. 5A-5B.

FIGS. 5A-5C are diagrams illustrating exemplary features that may be associated with therapeutic bra 10'. Certain components of the therapeutic bra 10' are as described above in connection with the therapeutic bra 10, except as noted herein. Those components bear similar reference characters to the components of the therapeutic bra 10, but with a primed suffix ('). In some embodiments of therapeutic bra 10', there may be at least one flap 50 coupled to at least a portion of the body portion 12'. In some embodiments, the first and second heating apparatuses described herein are associated with the flap 50. The flap 50 is configured to conceal the first opening 32 and the second opening 42 and/or other portions of the bra or user. The flap 50 may be comprised of the textile 61' of the body portion 12'.

The flap 50 of therapeutic bra 10' may further comprise a first flap 52 and a second flap 54, wherein the first slit 55 is disposed on the first flap 52 and the second slit 57 is disposed on the second flap 54. The first flap 52 and the second flap 54 may be separate, joined at the center, and/or one piece. In some embodiments the first and second heating apparatuses are each associated with the first flap 42 and/or the second flap 54, respectively. The flap 50 includes the following portions (described in a closed position as shown in FIG. 5A) a first upper portion 33f located at the top and adjacent to the neckline of the user and strap 19a, a first lower portion 35f located at the bottom, a first side portion 36f adjacent to the first side 18', a center bridge 35fc between the first flap 52 and second flap 54, the second upper portion 43f located at the top and adjacent to the neckline of the user and strap 19b', a second lower portion 45f located at the bottom, and a second side portion 46f adjacent to the second side 20'.

The flap 50 may further comprise a first slit 55 and a second slit 57 for receiving a breast pump therethrough. The first slit 55 and the second slit 57 may be disposed in the flap 50 such that they are disposed adjacent to the first opening 32' of the first cup 30' and the second opening 42' of the second cup 40', respectively. In an exemplary embodiment, the first and second slits 55, 57, can each be disposed respectively in at least one of the following: the first lower portion 35f, the first side portion 36f, the second the lower portion 45f, and the second side portion 46f.

The therapeutic bra 10' may further comprise a plurality of fasteners 62 disposed on the flap 50 and a plurality of attachments 64 for said fasteners 62 disposed on the body portion 12'. In an embodiment, the attachments 64 are disposed on the front 14' of the body portion. The plurality of fasteners 62 and plurality of attachments 64 may be may be disposed on at least one of the following areas of the body portion 12': the first cup 30', the second cup 40', the band 22', the first strap 19a', the second strap 19b', a first upper portion 33', the first lower portion 35', the first side portion 36', the center bridge 35c, the second upper portion 43', the second lower portion 45', and the second side portion 46'. The plurality of fasteners 62 and plurality of attachments 64 may be may be disposed on at least one of the following areas of the flap 50: the first upper portion 33f, the first lower portion 35f, the first side portion 36f, the center bridge 35fc, the second upper portion 43f, the second lower portion 45f, and the second side portion 46f. In an embodiment, as shown in FIG. 5A, the fasteners 62 are disposed on an interior surface 50s of the flap 50. In FIG. 5A, the fasteners 62 are dashed to show their respective location on the outer periphery of the interior surface 50s of the flap 50.

As shown in FIG. 5B, the fasteners 62 may be configured to allow the flap 50 to selectively conceal or expose the first opening 32' and the second opening 42' by attaching to or detaching from the attachments 64. In FIG. 5B the flap 50 is shown in a partially open position with the first flap pulled away to expose the first cup 30', which shows the plurality of fasteners 62 on the interior surface 50s of the flap 50 as well as some of the plurality attachments 64 disposed on the body 12' the first strap 19a', the first lower portion 35', the center bridge 35c', and the first side portion 36'. The second flap 54 is shown in the covered position and partially attached to the body portion; however, it is contemplated that the user could completely remove the flap 50 from the body portion 12'.

The therapeutic bra 10' may further comprise flap neckline 24f defined by the top edge of the flap 50. As shown in FIG. 5A, the bra 10' includes a latitudinal midline M that evenly divides the front 14' of bra 10' into a top half $M_1$ having the straps 19a', 19b', and a bottom half $M_2$ having a neckline 24f defined by the top or upper edge of the flap 50. The top half $M_1$ includes a topmost point Mt in the respective strap 19a', 19b' (e.g., the top of the strap at the top of the user's shoulder). The bottom half $M_2$ includes a bottom most point $M_b$ of the band 22' (e.g., the bottom edge) or, in embodiments without a band 22', at the first and second lower portions 35', 45'. In the exemplary embodiment shown in FIG. 3A, the flap neckline 24f is substantially aligned with the latitudinal midline M. In other embodiments, having a higher neckline 24f the flap neckline 24 is above the latitudinal midline M. In an exemplary embodiment of a high flap neckline 24f, the flap neckline 24f is disposed in the top half $M_1$ of the bra. In some embodiments, the flap neckline 24f may extend to approximately an inch below the user's collarbones so that the flap 50 covers the entire breast tissue on the chest of the user.

The therapeutic bra 10' may further comprise a cup neckline 24c defined by the top edge of the first and second cups 30', 40'. As shown in FIG. 5B, the bra 10' includes a latitudinal midline M that evenly divides the front 14' of bra 10' into a top half $M_1$ having the straps 19a, 19b, and a bottom half $M_2$ having the band 22'. The cup neckline 24c is defined by the top or upper edge of the first and second cups 30, 40 (only the first cup 30 is shown in the open position, it should be understood that the cup neckline 24c on the second cup 40 is substantially similar to that of the first cup 30). The cup neckline 24c can form substantially a "V" shape in the center to provide a cup coverage (which is less than full coverage of the user). The top half $M_1$ includes a topmost point Mt in the respective strap 19a', 19b' (e.g., the top of the strap at the top of the user's shoulder). The bottom half $M_2$ includes a bottom most point $M_b$ of the band 22 (e.g., the bottom edge) or, in embodiments without a band 22, at the bottom of the first and second lower portions 35', 45'. In the exemplary embodiment shown in FIG. 5B, the cup neckline 24c is substantially above the latitudinal midline M. In an exemplary embodiment of a cup neckline 24c, the cup neckline 24c is substantially disposed in the top half $M_1$ of the bra 10'. In some embodiments, the higher cup neckline 24c may extend to approximately an inch below the user's collarbones so that the front 14' covers the entire breast tissue on the chest of the user. In other embodiments, the cup neckline 24c is substantially disposed in the bottom half $M_2$ of the bra 10'.

FIG. 5C is a diagram illustrating the center layer 65' of the flap 50 of FIGS. 5A-5B. Referring to FIG. 5C, the first heating loop 72' may be further interwoven through the center layer 65' of the flap 50 to form hairpin curves in a radial pattern circumferentially around the first slit 55, and the second heating loop 82' may be further interwoven through the center layer 65' of flap 50 to form hairpin curves in a radial pattern circumferentially around the second slit 57; however, the first and second heating loops 72', 82' may be configured with various patterns as needed to provide the heating necessary for treatment of the user. As shown in this embodiment, the first and/or second heating loops 72', 82' can be disposed in the first cup 30', second cup 40', and to the flap neckline 24f in the top half $M_1$ of the front 14 of the bra 10'.

In other embodiments, the first heating loop 72' and the second heating loop 82' may be interwoven through the center layer 65' of the flap 50, concentrically around the first slit 55 and the second slit 57, respectively.

Alternatively, the first heating loop 72' and the second heating loop 82' may be interwoven through the center layer 65' of the flap 50 in various patterns or to form an irregular path through the center layer 65'.

Figure 6A:
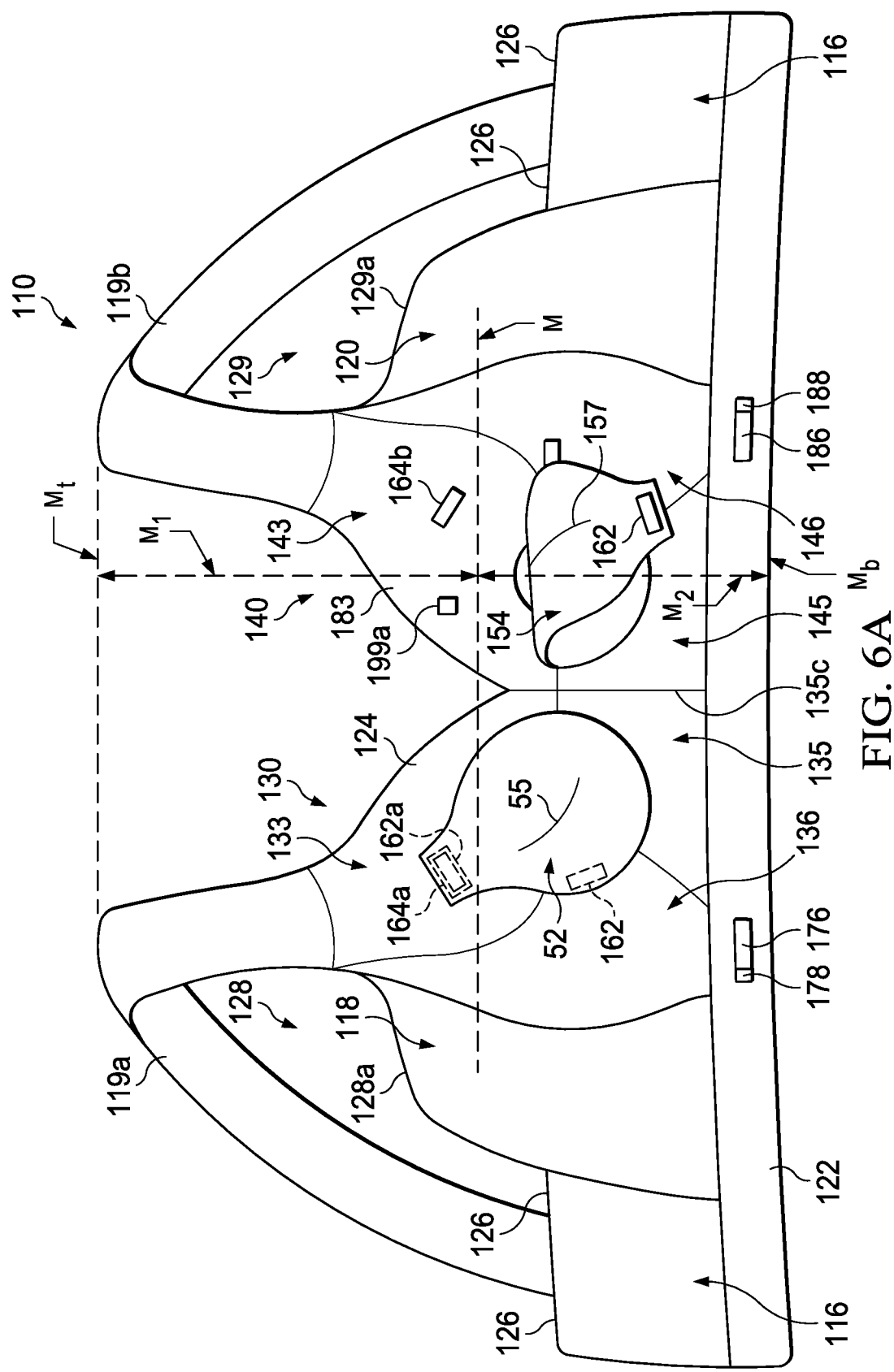
FIG. 6A is a diagram illustrating an exemplary embodiment of a therapeutic bra.
Figure 6B:
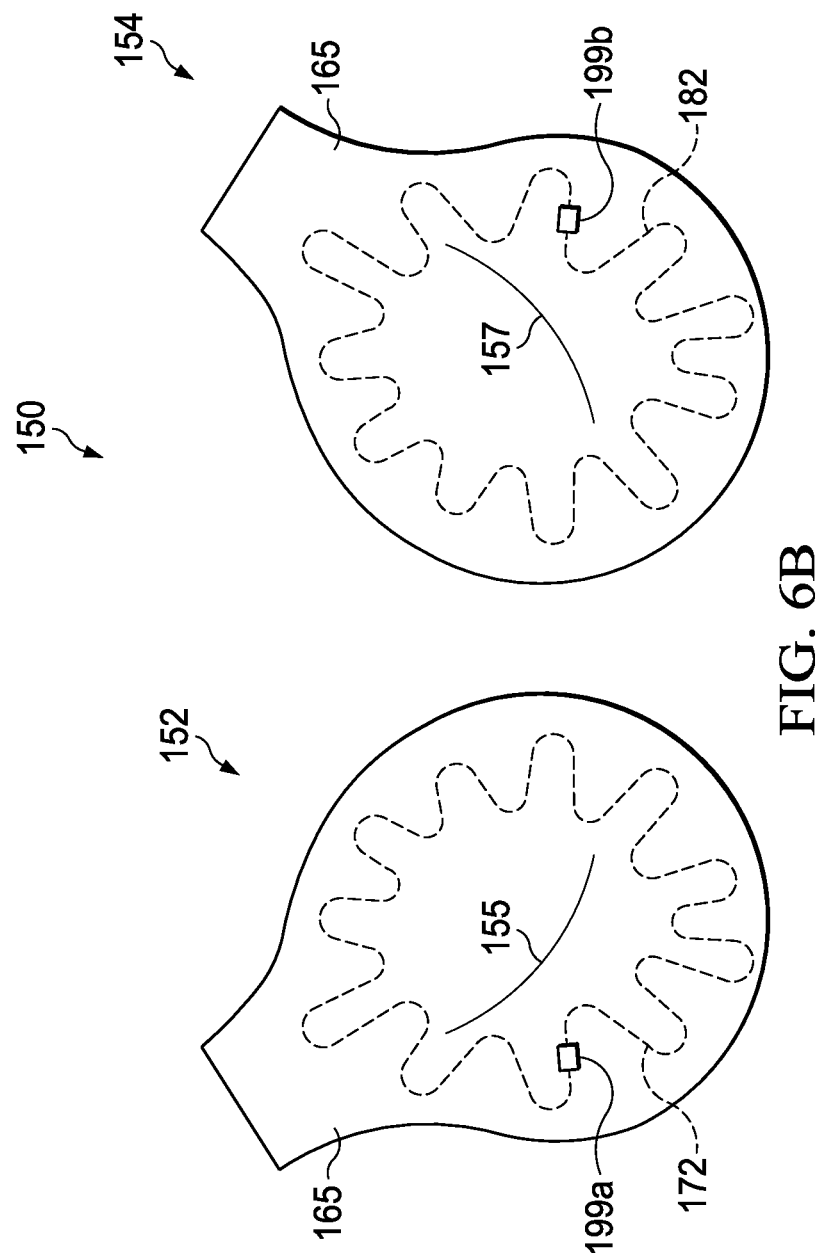
FIG. 6B is a diagram illustrating an internal view of the center layer of the flaps of FIG. 6A.

FIGS. 6A-6B illustrate another example of a therapeutic bra 110. Certain components of the therapeutic bra 110 are as described above in connection with the therapeutic bra 10, 10', except as noted herein. Those components bear similar reference characters to the components of the therapeutic bra 10, 10' but with a leading '1'. In some illustrative embodiments of a therapeutic bra 110, a first flap 152 may be coupled to the first cup 130 at the first lower portion 135, as seen in FIG. 6A. A second flap 154 may be coupled to the second cup 40 at the second lower portion 45. A first fastener 162a may be disposed on an edge of the first flap 152 in the first upper portion 133f and a second fastener 162b may be disposed on an edge of the second flap 154 in the second upper portion 143f. A first attachment 164a may be disposed on the first upper portion 133 and a second attachment 164b may be disposed on the second upper portion 143. The first fastener 162a may be configured to selectively conceal or expose opening 132 (not shown) by connecting to or disconnecting from the first attachment 164a. The second fastener 162b may be configured to selectively conceal or expose the second opening 142 (partially shown) by connecting to or disconnecting from the second attachment 164b. As seen in FIG. 6A, the first fastener 162a and second attachment 164a are connected to conceal opening 132 and the second fastener 162b and second attachment 164b are disconnected to partially expose opening 142.

In some embodiments of the therapeutic bra 110, the flap 50 may comprise a first flap 152 and a second flap 154. The first flap 152 may be coupled to the first cup 30 at the first side portion 36, adjacent to the first side 18. The second flap 154 may be coupled to the second cup 40 at the second side portion 46, adjacent to the second side 20.

The therapeutic bra 110 may further comprise a neckline 124 defined by the top edge of the first and second cups 130, 140. As shown in FIG. 5B, the bra 110 includes a latitudinal midline M that evenly divides the front 114 of bra 110 into a top half $M_1$ having the straps 119a, 119b, and a bottom half $M_2$ having the band 122. The neckline 124 is defined by the top or upper edge of the first and second cups 30, 40. In the exemplary embodiment shown in FIG. 6A, the neckline 124 is substantially above the latitudinal midline M. For example, 80% or more of the neckline 124 is above the latitudinal midline M. In an exemplary embodiment of the neckline 124, the neckline 124 is substantially disposed in the top half $M_1$ of the bra 110. In some embodiments, the neckline 124 extends completely in the top half $M_1$ of bra 110.

FIG. 6B is a diagram illustrating the center layer 165 of an exemplary embodiment of a first flap 152 and the second flap 154 of FIG. 6A. Referring to FIG. 6B, the first heating loop 172 may be further interwoven through the center layer 165 of the first flap 152 to form hairpin curves in a radial pattern circumferentially around the first slit 155, and the second heating loop 182 may be further interwoven through the center layer 165 of second flap 154 to form hairpin curves in a radial pattern circumferentially around the second slit 157. In other embodiments, the first heating loop 172 and the second heating loop 182 may be interwoven through the center layer 165 of the first flap 152 and the second flap 154, concentrically around the first slit 55 and the second slit 57, respectively. Alternatively, the first heating loop 172 and the second heating loop 182 may be interwoven through the center layer 165 of the first flap 152 and the second flap 154 in various patterns or to form an irregular path through the center layer 165.

Figure 7A:
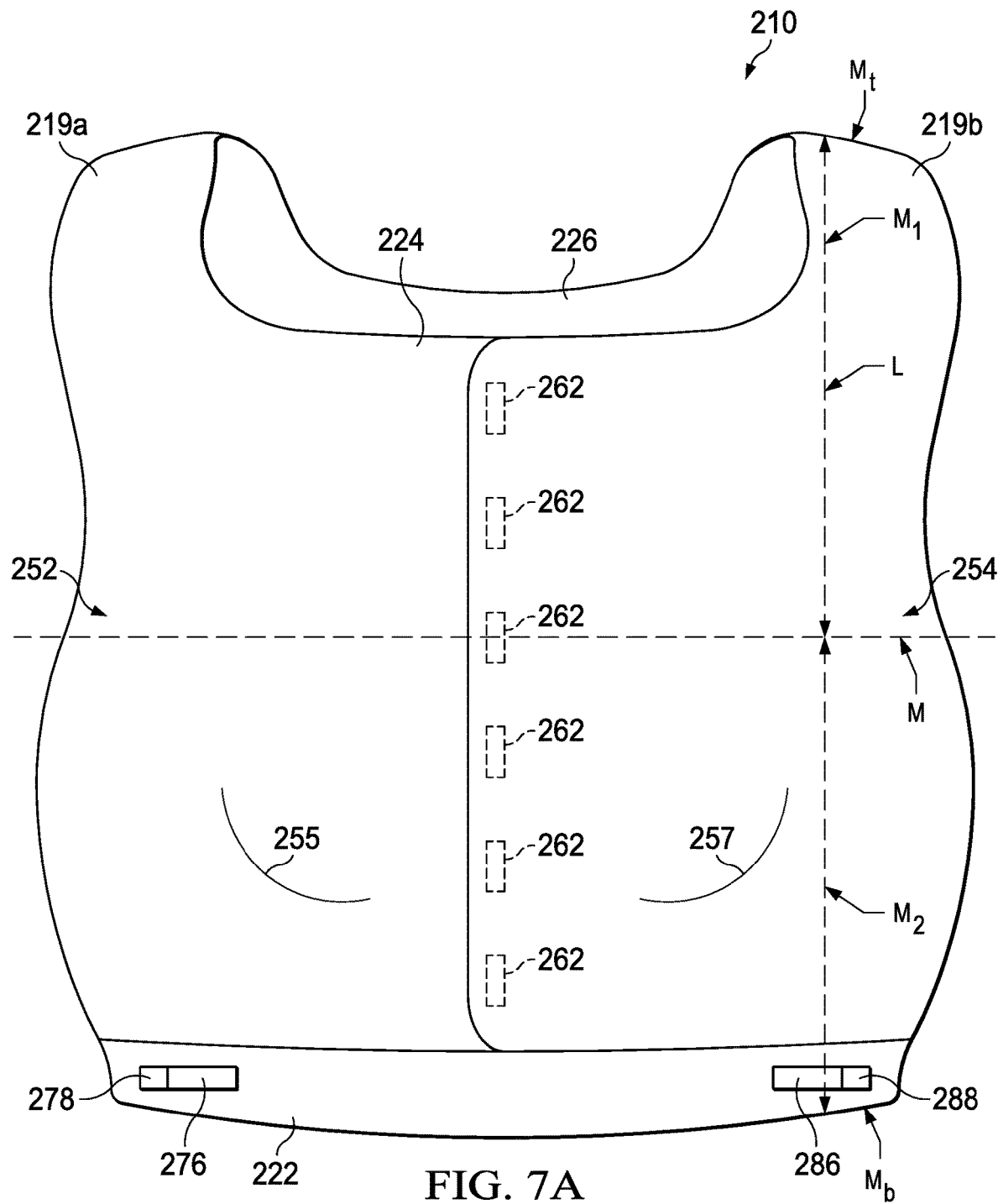
FIG. 7A is a diagram illustrating an exemplary embodiment of a therapeutic bra.
Figure 7B:
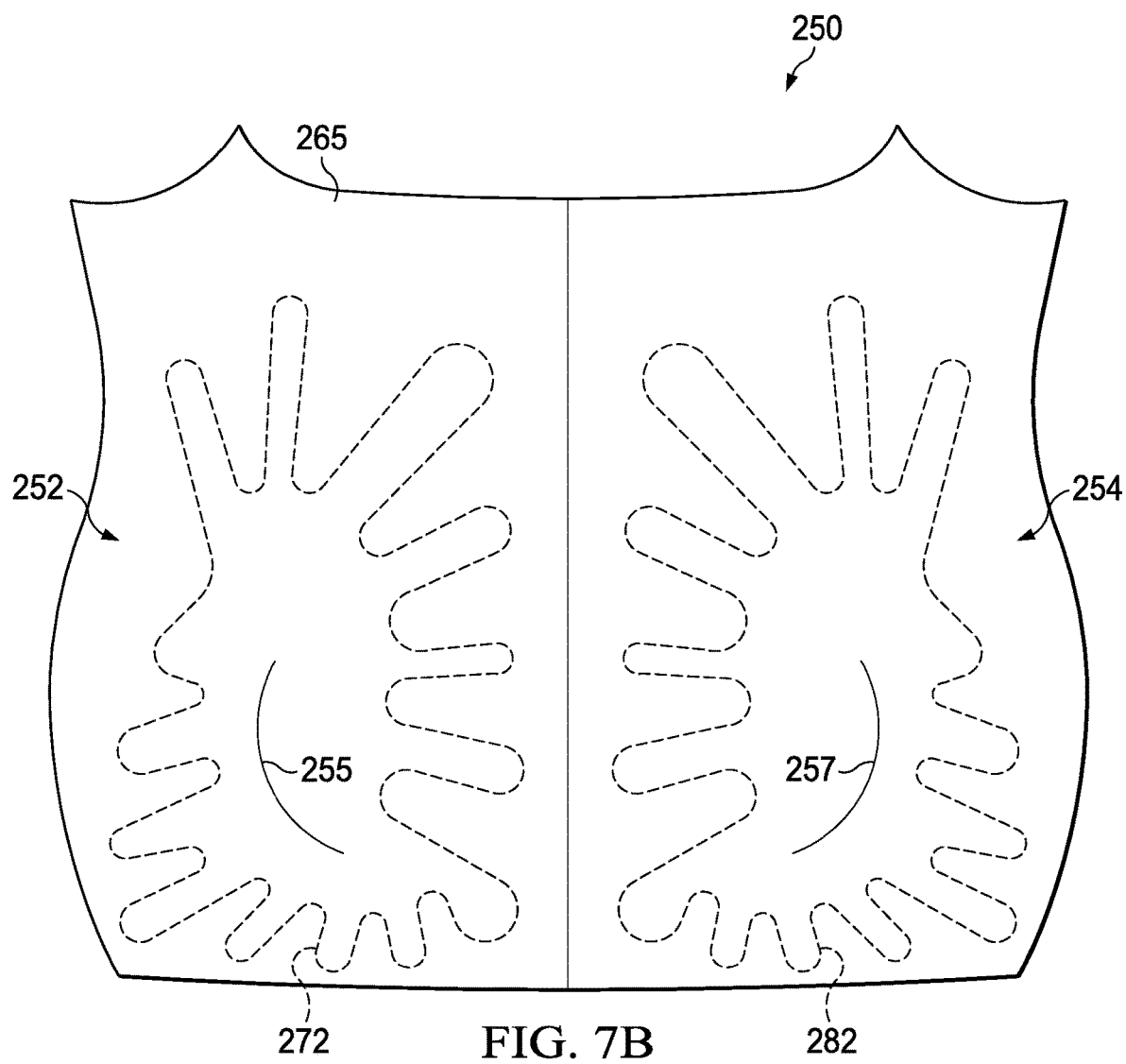
FIG. 7B is a diagram illustrating an internal view of the center layer of the flaps of FIG. 7A.

FIGS. 7A-7B illustrate another example of a therapeutic bra 210. Certain components of the therapeutic bra 210 are as described above in connection with the therapeutic bra 110, except as noted herein. Those components bear similar reference characters to the components of the therapeutic bra 110, but with a leading '2' rather than a leading T. Referring to FIG. 7A, the therapeutic bra 210 includes a plurality of fasteners 262 disposed on the second flap 254 and a plurality of attachments 264 disposed on the first flap 252. The plurality of fasteners 262 disposed on the second flap 254 may be connected or disconnected to the plurality of attachments 264 on the first flap 252 to conceal or expose the body portion 212, first opening 232, and second opening 242.

The therapeutic bra 210 of FIG. 7A may further comprise a neckline 224 defined by the top edge of the first flap 252 and the second flap 254 when the fasteners 262 are connected to the attachments 264. In the illustrative embodiment, the neckline 224, defined by the tops of the first and second flaps 252, 254, is substantially above the latitudinal midline M and adjacent to collarbones of the user. For example, 100% of the neckline 224 is above the latitudinal midline M. In the embodiment shown in FIG. 7A, the neckline 224 is disposed substantially adjacent to the topmost point Mt in the straps 219a, 219b. In an exemplary embodiment of the neckline 224, the neckline 224 is substantially disposed in the top half $M_1$ of the bra 210. Advantageously, the bra 210 is configured so that the body portion 212, the first flap 252, and the second flap 254 with the high or full coverage neckline 224 covers the entire breast tissue on the chest of the user (e.g., this embodiment provides therapeutic heat and/or vibration to the Spence space of the breast tissue as well as the top two quadrants of the breast that reach the second rib just below the clavicle (during lactation the breast tissue expands to fill these spaces).

FIG. 7B is a diagram illustrating a flap 250 comprising a center layer 265 of the first flap 252 and the second flap 254 of FIG. 7A. Referring to FIG. 7B, the first heating loop 272 may be further interwoven through the center layer 265 of the first flap 252 to form hairpin curves in a radial pattern circumferentially around the first slit 255, and the second heating loop 282 may be further interwoven through the center layer 265 of second flap 254 to form hairpin curves circumferentially around the second slit 257. In other embodiments, the first heating loop 272 and the second heating loop 282 may be interwoven through the center layer 265 of the first flap 252 and the second flap 254, concentrically around the first slit 255 and the second slit 257, respectively. Alternatively, the first heating loop 272 and the second heating loop 282 may be interwoven through the center layer 265 of the first flap 252 and the second flap 254 in various patterns or to form an irregular path through the center layer 265.

Figure 8B:
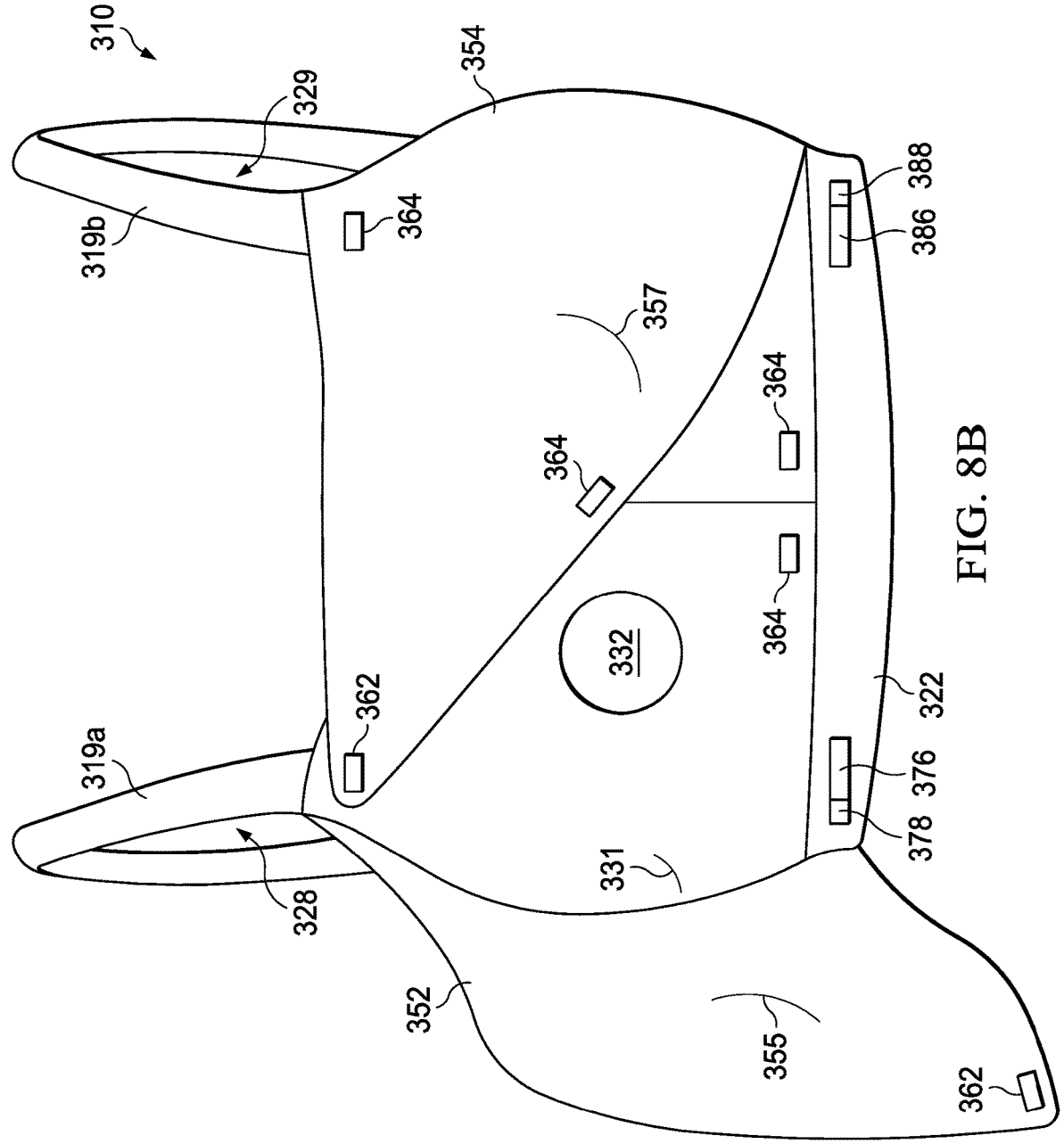
Figure 9:
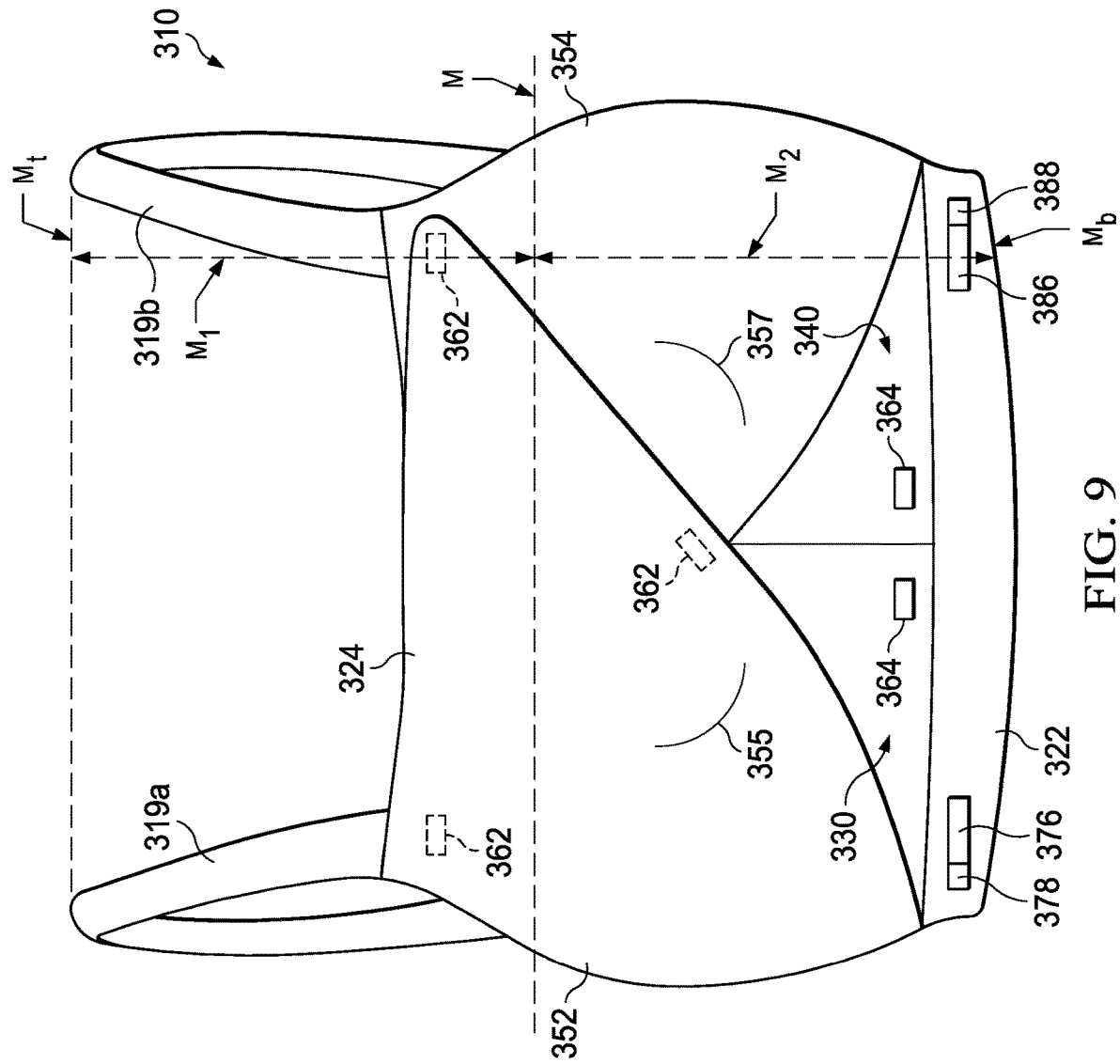

FIGS. 8A-8C, 9, and 10 illustrate another example of a therapeutic bra 310. Certain components of the therapeutic bra 310 are as described above in connection with the therapeutic bra 210, except as noted herein. Those components bear similar reference characters to the components of the therapeutic bra 210, but with a leading '3' rather than a leading '2'. Advantageously, the therapeutic bra 310 provides a neckline that is adjustable as well as adjustable positioning of the first and second heating loops 372, 382 by the user. The user can modify the coverage of the therapeutic bra 310 by positioning the first flap and/or second flap 352, 354 via the various locations of the plurality of fasteners 362 and plurality of attachments 364. In an exemplary embodiment, the therapeutic bra 310 is adjustable to a full coverage provided by neckline 324 to provide the heat therapy and/or vibration therapy to the Spence space of the breast tissue as well as the top two quadrants of the breast that reach the second rib just below the clavicle, as shown in FIGS. 8B and 9, as well as a cup coverage provided by cup neckline 324c, as shown in FIG. 10 (e.g., forming substantially a "V" shape in the center).

Referring to FIG. 8A, in some embodiments of therapeutic bra 310 the flap 350 may further comprise a first flap 352 and a second flap 354 that can be configured to provide a therapeutic heat and/or vibration output. The first flap 352 may be coupled to the first cup 330 at the first side portion 336 and may be configured to expose the first opening 332 when folded sideways towards the first arm hole 328. The second flap 354 may be attached to the second cup 340 at the second side portion 346 and may be configured to expose the second opening 342 when folded sideways towards the second arm hole 329.

Referring now to FIGS. 8A and 8C, the first heating loop 372 may be interwoven through a center layer 365 of the front 314 of the body portion and, in particular, the first cup 330, in a concentrically arranged pattern around the first opening 332. The second heating loop 382 may be interwoven through the center layer 365 of the front of the body portion 314, and, in particular, the second cup 340, in a concentrically arranged pattern around the second opening 342.

The first heating loop 372 can be operatively connected to a third heating loop 373. The third heating loop 373 can heat the first side 318 and/or first flap 352. The third heating loop 373 may be interwoven through the center layer 365 of the first side 318 and the first flap 352, in a concentrically arranged pattern around the first slit 355. The second heating loop 382 can be operatively connected to a fourth heating loop 383. The fourth heating loop 383 can heat the second side 320 and/or second flap 354. The fourth heating loop 383 may be interwoven through the center layer 365 of the second side 320 and second flap 354, in a concentrically arranged pattern around the second slit 357.

The plurality of fasteners 362 and the plurality of attachments 364 may be disposed on the first flap 352, the second flap 354, and the body portion 312 such that the first flap 352 and the second flap 354 may be connected to the body portion 312 to provide multiple necklines (e.g., adjustable neckline). FIG. 9 is a diagram illustrating exemplary features of the therapeutic bra 310 of FIGS. 8A and 8B. In FIG. 9, the fasteners 362 may be connected to the attachments 364 to form a high neckline 324 providing full coverage that extends to approximately one inch below the user's collarbones so that the body portion 312, the first flap 352, and the second flap 354 cover the entire breast tissue on the chest of the user. The bra 310 includes a latitudinal midline M that evenly divides the front 314 of bra 310 into a top half $M_1$ having the straps 319a, 319b, and a bottom half $M_2$ having the first and second lower portions 335, 345, and/or the band 322. The top half $M_1$ includes a topmost point Mt in the respective strap 319a, 319b (e.g., the top of the band at the top of the user's shoulder). The bottom half $M_2$ includes a bottom most point $M_b$ of the band 322 (e.g., the bottom edge) or, in embodiments without a band 222, at the bottom of the first and second lower portions 335, 345. In the exemplary embodiment, the neckline 324 is above the latitudinal midline M for a high or full coverage neckline. In an embodiment, the neckline 324 is disposed in the top half $M_1$ of the bra 310. In some embodiments, the neckline 324 may extend to approximately an inch below the user's collarbones so that the front 314 covers the entire breast tissue on the chest of the user. Advantageously, the full coverage and/or higher neckline 324 as described herein provides therapeutic heat and/or vibration to the Spence space of the breast tissue as well as the top two quadrants of the breast that reach the second rib just below the clavicle (during lactation the breast tissue expands to fill these spaces).

FIG. 10 is a diagram illustrating exemplary features of the therapeutic bra 310 of FIGS. 8A-9. In FIG. 10, the fasteners 362 may be connected to the attachments 364 to such that the first flap 352 and second flap define a cup neckline 324c. In the embodiment shown, the cup neckline 324c substantially aligns with the neckline 324 defined by first and second cups 330, 340. In other embodiments, the cup neckline 324c can be above or below the neckline 324 as configured by the user. In the exemplary embodiment shown in FIG. 10, the cup neckline 324c is about 50% above the latitudinal midline M. Advantageously, the cup neckline 324c is adjustable to provide varying amounts of coverage for the user, which permits the user to adjust the position of the heating loops 72, 82 as needed to treat the condition (e.g., mastitis, assisting with let-down, weaning, etc.).

FIGS. 11A-11B illustrate another embodiment of a therapeutic bra 410. Certain components of the therapeutic bra 410 are as described above in connection with the therapeutic bra 310, except as noted herein. Those components bear similar reference characters to the components of the therapeutic bra 310, but with a leading '4' rather than a leading '3'. FIG. 11A is a diagram of an example embodiment of a therapeutic bra 410 which has a body portion 412 with a first side 418 and a second side 420. The body portion 412 includes a front 414, a back 416, a first side portion 436, a second side portion 446, a first lower portion 435 disposed adjacent to the band 422 on the first side 418, and a second lower portion 445 disposed adjacent to the band 422 on the second side 420. The first and second lower portions 435, 445 provide coverage to a portion of the user's chest but is without a cup or dome shape. This version has no upper portions so there is no hole but rather the entire breast area is exposed when the first flap 452 and second flap 454 are opened towards the first and second armpits. The first flap 452 is attached to the first side 418 at the first side portion 436 so that when it is configured to expose the first breast, it folds sideways towards the first armpit. The second flap 454 is attached to the second side 420 at the second side portion 446 so that when it is configured to expose the second breast, it folds sideways towards the second armpit. The first flap 452 is shown in the open configuration with the second flap 454 in the covered position. The first flap 452 and second flap 454 are substantially symmetrical; therefore, for the sake of the efficiency each flap will be disclosed to explain certain features that apply to both the first and second flaps 452, 454. The second flap 454 is attached to the second side portion 446 so that when it is configured to expose the second breast, it folds sideways towards the second armpit. The second flap 454 is attached to the first side 418 via fastener 462 to an upper corner attachment 464 adjacent to first armpit. The second flap 454 is attached to the second side 420 via fastener 462 secured to an attachment 462 disposed in the upper corner adjacent to the second armpit. The second flap 454 is also attached to the second side 420 via a fastener 462 secured to an attachment 464 in the second lower portion 445 and/or adjacent to or in the center bridge 435c of the body portion 412.

In some embodiments, the therapeutic bra 410 provides a neckline 424 that is adjustable as well as adjustable positioning of the first and second heating loops 472, 482 by the user. The user can modify the coverage of the therapeutic bra 410 by positioning the first flap and/or second flap 452, 454 via the various locations of the plurality of fasteners 462 and plurality of attachments 464. In an exemplary embodiment, the therapeutic bra 410 is adjustable to a full coverage provided by neckline 424, as shown in FIG. 11A, as well as a cup coverage provided by positioning the first and second flaps 452, 454 to provide a cup neckline as shown in the embodiment in FIG. 10 (e.g., forming substantially a "V" shape in the center). Advantageously, the full coverage and/or higher neckline 424 as described herein provides therapeutic heat and/or vibration to the Spence space of the breast tissue as well as the top two quadrants of the breast that reach the second rib just below the clavicle (during lactation the breast tissue expands to fill these spaces).

FIG. 11B is a diagram illustrating the center layer 465 of the flaps 450 (e.g., first flap 452 and the second flap 454) of FIG. 11A. The first heating loop 472 may be further interwoven through the center layer 465 of the first flap 452 to form an irregular path portion (e.g., branched) around the first slit 455, and the second heating loop 482 may be further interwoven through the center layer 465 of second flap 454 to form an irregular path portion (e.g., branched) around the second slit 457. In other embodiments, the first heating loop 472 and the second heating loop 482 may be interwoven through the center layer 465 of the first flap 452 and the second flap 454, concentrically around the first slit 455 and the second slit 457, respectively. Alternatively, the first heating loop 472 and the second heating loop 482 may be interwoven through the center layer 465 of the first flap 452 and the second flap 454 in various patterns or to form an irregular path through the center layer 465.

Figure 12:
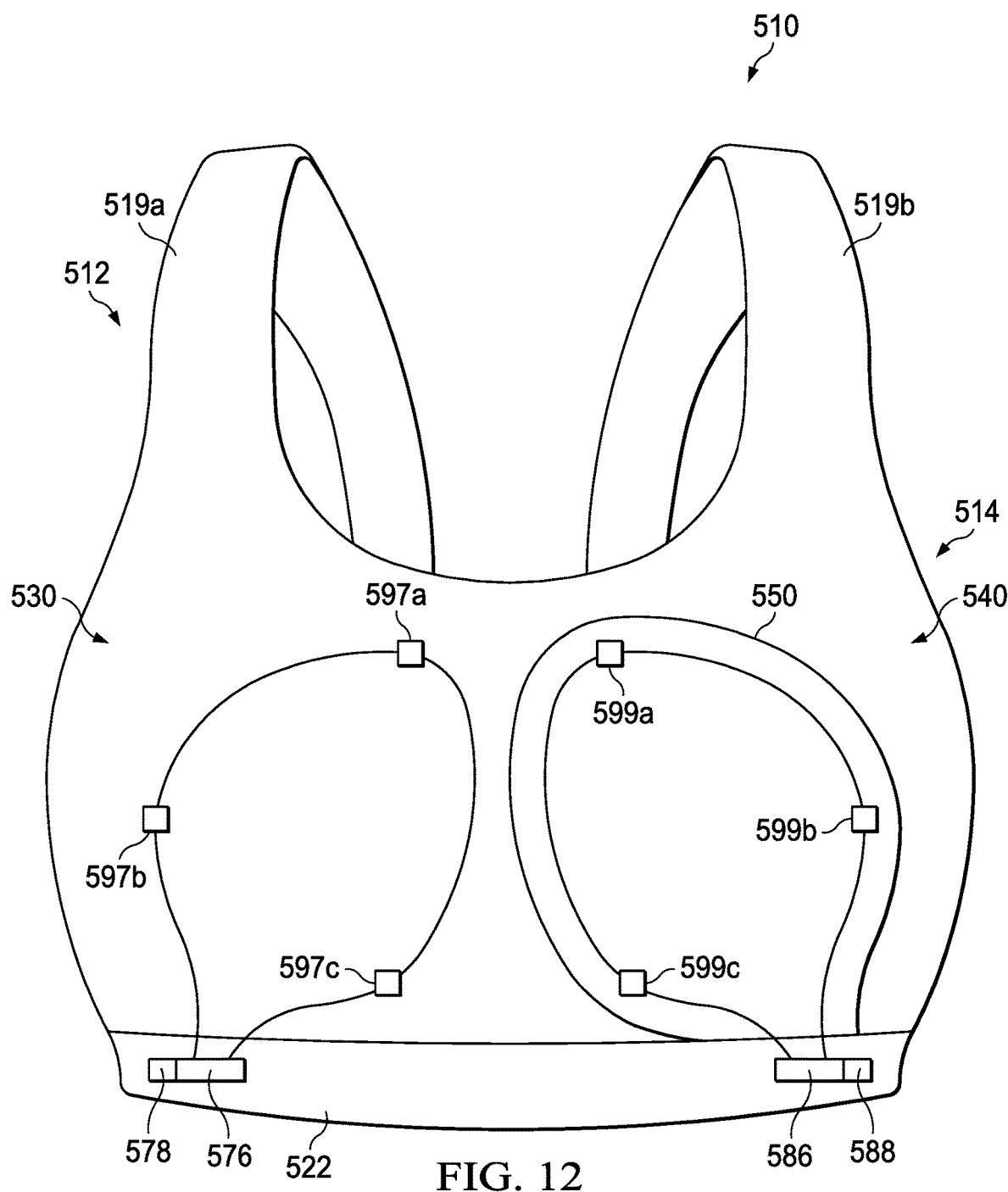
FIG. 12 is a diagram illustrating an embodiment of a therapeutic bra including a vibrating therapy device that can provide treatment in accordance with this specification.

FIG. 12 is still another schematic example of a therapeutic bra 510. Certain components of the therapeutic bra 510 are as described above in connection with the therapeutic bra 410, except as noted herein. Those components bear similar reference characters to the components of the therapeutic bra 410, but with a leading '5' rather than a leading '4'. Referring now to FIG. 12, an embodiment of therapeutic bra 510 including a plurality of vibrating devices 597 disposed in the first cup 530, the second cup 540, the first side 518, the second side 520, at least one flap 550 (e.g., a first flap and/or a second flap as described herein), and a combination thereof. In an exemplary embodiment, the plurality of vibrating devices 597 includes a first vibrating device 597a, a second vibrating device 597b, and a third vibrating device 597c associated with the front 514 of the body 512. In an embodiment, the plurality of vibrating devices 597 includes the first vibrating device 597a, the second vibrating device 597b, and the third vibrating device 597c associated with at least one cup (e.g., a first cup 530 and/or a second cup as described in embodiments herein); for example, the vibrating devices 597a, 597b, and 597c are disposed on the first cup 530. In an exemplary embodiment, the plurality of vibrating devices 597 also includes a fourth vibrating device 599a, a fifth vibrating device 599b, and a sixth vibrating device 599c associated with flap 550 (e.g., a first flap and/or a second flap as described in embodiments herein). During operation, physical vibration is externally applied to the user by at least one of the vibrating devices 597a, 597b, 597c, 599a, 599b, and/or 599c. In some embodiments, the plurality of vibrating devices 597 externally apply physical vibration to the user at the same time continuously. In some embodiments, the plurality of vibrating devices 597 externally apply physical vibration to the user sequentially by the vibrating devices 597a, 597b, 597c, 599a, 599b, 599c; for example, the first vibrating device 597a applies vibration first, the second vibrating device 597b applies vibration second, the third vibrating device 597c applies vibration third, etc. It will be understood by those skilled in the art that the actual sequence could be varied to treat different areas of the user. The vibrating devices can include low profile vibration elements so that the vibrating device is not visible when the user is clothed. Advantageously, the vibration applied to the breast tissue of the user by the vibrating devices can cause movement into the breast tissue to breakup and loosen trapped milk blocked by a clogged duct and/or help to physically move a blockage in the duct.

In some embodiments, some or all of the vibrating devices can be operated independently and powered by a battery therein and turned on by the user as needed (e.g., a power push button for each vibrating device).

In an illustrative embodiment, the first, second, and third vibrating devices 597a, 597b, and 597c, may be associated with the first electric circuit 570 and may be in electric connection with the first power source 576 and the first controller 578. The first controller 578 may be further configured to operate the first, second, and third vibrating devices 597a, 597b, and 597c, simultaneously and/or independently. Likewise, the fourth, fifth, and sixth vibrating devices 599a, 599b, and 599c, may be associated with the second electric circuit 580 and may be in electric connection with the second power source 586 and the second controller 588. The second controller 588 may be further configured to operate the fourth, fifth, and sixth vibrating devices 597d, 597e, and 597f, simultaneously and/or independently.

The terms "a" and "an" are defined as one or more unless this disclosure explicitly requires otherwise.

The term "substantially" is defined as largely, but not necessarily wholly, what is specified (and includes what is specified; e.g., substantially 90 degrees includes 90 degrees), as understood by a person of ordinary skill in the art. In any disclosed embodiment, the terms "substantially," "approximately," and "about" may be substituted with "within [a percentage] of" what is specified, where the percentage includes 0.1, 1, 5, and 10 percent.

Terms such as "first" and "second" are used only to differentiate features and not to limit the different features to a particular order or to a particular quantity.

Where numerical ranges or limitations are expressly stated, such express ranges or limitations should be understood to include iterative ranges or limitations of like magnitude falling within the expressly stated ranges or limitations (e.g., from about 1 to about 10 includes 2, 3, 4, etc.; greater than 0.10 includes 0.11, 0.12, 0.13, etc.). For example, whenever a numerical range with a lower limit, $R_l$, and an upper, $R_u$, is disclosed, any number falling within the range is specifically disclosed. In particular, the following numbers within the range are specifically disclosed: $R=R_l+k*(R_u-R_l)$, wherein k is a variable ranging from 1 percent to 100 percent with a 1 percent increment, i.e., k is 1 percent, 2 percent, 3 percent, 4 percent, 5 percent, . . . , 50 percent, 51 percent, 52 percent, . . . , 95 percent, 96 percent, 97 percent, 98 percent, 99 percent, or 100 percent. Any numerical range defined by two R numbers as defined in the above is also specifically disclosed and includes the two R numbers.

Use of the term "optional" with respect to any element of a claim means that the element is required, or alternatively, the element is not required, both alternatives being within the scope of the claim.

Use of broader terms such as comprises, includes, and has (and any derivatives of such terms, such as comprising, including, and having) should be understood to provide support for narrower terms, such as consisting of, consisting essentially of, and comprised substantially of. Thus, in any of the claims, the term "consisting of," "consisting essentially of," or "comprised substantially of" can be substituted for any of the open-ended linking verbs recited above in order to change the scope of a given claim from what it would otherwise be using the open-ended linking verb.

The same or similar features of one or more embodiments are sometimes referred to with the same reference numerals within a figure or among figures. However, one or more features having the same reference numeral should not be construed to indicate that any feature is limited to the characteristics of another feature having the same reference numeral, or that any feature cannot already have, or cannot be modified to have, features that are different from another feature having the same reference numeral.

At least one embodiment is disclosed and variations, combinations, and/or modifications of the embodiment(s) and/or features of the embodiment(s) made by a person having ordinary skill in the art are within the scope of the disclosure. Alternative embodiments that result from combining, integrating, and/or omitting features of the embodiment(s) are also within the scope of the disclosure. The feature or features of one embodiment may be applied to other embodiments to achieve still other embodiments, even though not described, unless expressly prohibited by this disclosure or the nature of the embodiments. The scope of protection is not limited by the description set out above but is defined by the claims that follow, the scope including all equivalents of the subject matter of the claims. Each and every claim is incorporated as further disclosure into the specification and the claims are embodiment(s) of the present invention.

The invention claimed is:

1. A therapeutic bra comprising:
   a body portion configured to fit around a back and chest of a user; the body portion having a front, a back, a first side, a second side, a first cup, and a second cup; the front and the back are connected at the first and second sides, the body portion extends circumferentially around the back and chest of the user, the first cup disposed on the front of the body portion, the first cup including a first opening for receiving a first nipple of the user therethrough;

the second cup disposed on the front of the body portion, the second cup including a second opening for receiving a second nipple of the user therethrough;

a first flap coupled to the front and configured to selectively conceal or expose the first opening;

a second flap coupled to the front and configured to selectively conceal or expose the second opening;

a first heating apparatus comprising:
  a first power source disposed on the body portion;
  a first controller disposed on the body portion; and
  a first heating loop operably connected to the first power source and the first controller; the first heating loop associated with at least one of the first cup, the first side, the front, and the first flap;

a second heating apparatus comprising:
  a second power source disposed on the body portion;
  a second controller disposed on the body portion; and
  a second heating loop operably connected to the second power source and the second controller; the second heating loop associated with at least one of the second cup, the second side, the front, and the second flap;

wherein the user can operate the first heating loop and the second heating loop in at least one of a simultaneous mode and an independent mode;

wherein the front comprises a full-coverage neckline such that when worn by the user, the front is adapted to cover the upper chest of the user, extending to approximately one inch below the collarbone of the user;

wherein the first side and the second side are adapted to extend to the creases of the armpits of the user;

wherein the first heating loop is at least partially disposed within the first side and extends along the upper edge and the lower edge of the first side; and wherein the second heating loop is at least partially disposed within the second side and extends along the upper edge and the lower edge of the second side.

2. The therapeutic bra according to claim 1, wherein the first and second heating loops are each comprised of an electrically conductive fiber that is malleable and with a low profile.

3. The therapeutic bra according to claim 2, wherein the electrically conductive fiber is at least one of the following: a nichrome resistance wire, a kanthal wire, a cupronickel alloy wire, a molybdenum disilicide wire, a positive temperature coefficient ceramic element, a conductive thread, and a carbon nanotube coated thread.

4. The therapeutic bra according to claim 2, wherein at least one of the body, the first flap, and the second flap are comprised of a textile having a non-conductive fiber, the electrically conductive fibers of the first and second heating loops are stitched through the textile.

5. The therapeutic bra according to claim 1, wherein the body, the first flap, and the second flap are each comprised of a multi-layer textile.

6. The therapeutic bra according to claim 5, wherein the multilayer textile comprises an inner layer, an outer layer, and a center layer, and at least one of the first heating loop and the second heating loop is woven through at least one of the inner layer, the outer layer, and the center layer.

7. The therapeutic bra according to claim 6, wherein the first and second heating loops are woven through the center layer.

8. The therapeutic bra according to claim 1, wherein the first heating loop and the second heating loop are at least partially disposed along the top edge of the full coverage neckline.

9. The therapeutic bra according to claim 8, wherein the first and second heating loop are adapted to provide heat directly to the Spence space of the breast tissue of the user.

10. The therapeutic bra according to claim 9, wherein the first and second heating loop are further adapted to provide heat directly to the area between the clavicle and the second rib of the user.

11. The therapeutic bra according to claim 8, wherein the first heating loop further comprises multiple hairpin curves disposed within the first side and the second heating loop further comprises multiple hairpin curves disposed within the second side.

12. The therapeutic bra according to claim 11, wherein the first heating loop further comprises multiple hairpin curves disposed within the front and the second heating loop further comprises multiple hairpin curves disposed within the front.

13. The therapeutic bra according to claim 1, wherein at least one of the first flap and the second flap includes a first slit and a second slit, respectively, the first slit being centrally positioned above the first opening and the second slit being centrally positioned above the second opening.

14. The therapeutic bra according to claim 1, further comprising a plurality of vibrating devices associated with at least one of the front, the first side, the second side, the first flap, and the second flap, wherein each of the vibrating devices are operated in at least one of a simultaneous mode and an independent mode.

15. A therapeutic bra comprising:
  a body portion configured to fit around a back and chest of a user; the body portion having a front, a back, a first side, a second side, a first cup, and a second cup; the front and the back are connected at the first and second sides, the body portion extends circumferentially around the back and chest of the user,
  the first cup disposed on the front of the body portion, the first cup including a first opening for receiving a first nipple of the user therethrough;
  the second cup disposed on the front of the body portion, the second cup including a second opening for receiving a second nipple of the user therethrough;
  a first flap coupled to the first cup and configured to selectively conceal or expose the first opening;
  a second flap coupled to the second cup and configured to selectively conceal or expose the second opening;
  a first heating apparatus comprising a first heating loop operably connected to a power source and a controller disposed on the body portion; the first heating loop associated with at least one of the first cup, the first side, the front, and the first flap; and
  a second heating apparatus comprising: a second heating loop operably connected to the power source and the controller; the second heating loop associated with at least one of the second cup, the second side, the front, and the second flap;
  wherein the front comprises a full-coverage neckline such that when worn by the user, the front is adapted to cover the upper chest of the user, extending to approximately one inch below the collarbone of the user;

wherein the first side and the second side are adapted to extend to the creases of the armpits of the user;

wherein the first heating loop is at least partially disposed within the first side and extends along the upper edge and the lower edge of the first side; and wherein the second heating loop is at least partially disposed within the second side and extends along the upper edge and the lower edge of the second side.

16. The therapeutic bra according to claim 15, wherein at least one of the body, the first flap, and the second flap are comprised of a textile having a non-conductive fiber, the first and second heating loops each comprise an electrically conductive fiber stitched through the textile.

17. The therapeutic bra according to claim 15, further comprising a plurality of vibrating devices disposed within the first side and the second side.

18. The therapeutic bra according to claim 17, wherein the first heating loop and the second heating loop are at least partially disposed along the top edge of the full coverage neckline.

19. A therapeutic bra comprising:
a body portion configured to fit around a back and chest of a user; the body portion having a front, a back, a first side, and a second side; the front and the back are connected at the first and second sides, the body portion extends circumferentially around the back and chest of the user;
a first opening for receiving a first nipple of the user therethrough, the first opening being disposed on the front of the body portion;
a second opening for receiving a second nipple of the user therethrough, the second opening being disposed on the front of the body portion;
a first flap coupled to the front of the body portion and configured to selectively conceal or expose the first opening;
a second flap coupled to the front of the body portion and configured to selectively conceal or expose the second opening;
a first heating apparatus associated with the first flap, the first heating apparatus comprising:
a first power source;
a first controller; and
a first heating loop operably connected to the first power source and the first controller; the first heating loop associated with the first flap;
a second heating apparatus associated with the second flap, the second heating apparatus comprising:
a second power source;
a second controller; and
a second heating loop operably connected to the second power source and the second controller; the second heating loop associated with the second flap;
wherein the user can operate the first heating loop and the second loop in at least one of a simultaneous mode and an independent mode;
wherein the front comprises a full-coverage neckline such that when worn by the user, the front is adapted to cover the upper chest of the user, extending to approximately one inch below the collarbone of the user;
wherein the first side and the second side are adapted to extend to the creases of the armpits of the user;
wherein the first heating loop is at least partially disposed within the first side and extends along the upper edge and the lower edge of the first side; and
wherein the second heating loop is at least partially disposed within the second side and extends along the upper edge and the lower edge of the second side.

20. The therapeutic bra according to claim 19, wherein the first heating loop further comprises multiple hairpin curves disposed within the front and the second heating loop further comprises multiple hairpin curves disposed within the front.

\* \* \* \* \*